US009643223B2

(12) United States Patent
Smith et al.

(10) Patent No.: US 9,643,223 B2
(45) Date of Patent: *May 9, 2017

(54) BIOREMEDIATION ENHANCING AGENTS AND METHODS OF USE

(75) Inventors: Donovan N. Smith, Parkville, MO (US); Michael R. Sieczkowski, Lenexa, KS (US); Wayne H. Wilke, Leawood, KS (US)

(73) Assignee: JRW Bioremediation, LLC, Lenexa, KS (US)

( * ) Notice: Subject to any disclaimer, the term of this patent is extended or adjusted under 35 U.S.C. 154(b) by 2124 days.

This patent is subject to a terminal disclaimer.

(21) Appl. No.: 12/049,959

(22) Filed: Mar. 17, 2008

(65) Prior Publication Data

US 2008/0227179 A1    Sep. 18, 2008

Related U.S. Application Data

(60) Provisional application No. 60/895,340, filed on Mar. 16, 2007, provisional application No. 60/914,524, filed on Apr. 27, 2007, provisional application No. 60/972,455, filed on Sep. 14, 2007.

(51) Int. Cl.
    *B09C 1/00* (2006.01)
    *B09C 1/10* (2006.01)
    *C02F 3/34* (2006.01)

(52) U.S. Cl.
    CPC ............... *B09C 1/10* (2013.01); *B09C 1/002* (2013.01); *C02F 3/34* (2013.01)

(58) Field of Classification Search
    CPC ...... C12P 1/02; C12P 7/06; C12P 7/08; C12P 19/00; C12P 8/047; A21D 8/047; A21D 10/025; A21D 2/265; A21D 6/001; A21D 8/02; A21D 8/042; A61F 13/42; A61F 2013/424; Y02E 50/17; C07C 29/76; C07C 31/04; C07C 31/08; B01D 3/00; C02F 3/34; C02F 1/68; C02F 1/70; C02F 1/705; C02F 1/72; C02F 2101/003; C02F 2101/20; C02F 2101/306; C02F 2101/32; C02F 2101/322; C02F 2101/36; C02F 2305/06; C02F 3/30; C02F 2101/12; C02F 2101/163; C02F 2303/02; C02F 3/308; C02F 3/348; C02F 2101/105; C02F 2101/16; C02F 2101/34; C02F 2301/08; C02F 2301/106; C02F 2303/20; C02F 3/06; C02F 3/085; C02F 1/66; C02F 1/683; C02F 2103/10; C02F 3/327; B09C 1/002; B09C 1/10; B09C 1/08; C12C 11/07; C12C 11/075; C12C 11/09
    See application file for complete search history.

(56) References Cited

U.S. PATENT DOCUMENTS

| 4,156,647 A | 5/1979 | Nieuwenhuis |
| 4,401,569 A | 8/1983 | Jahaveri et al. |
| 4,585,482 A | 4/1986 | Tice et al. |
| 5,006,250 A | 4/1991 | Roberts et al. |
| 5,071,754 A | 12/1991 | Walkup et al. |
| 5,089,123 A | 2/1992 | DeVoe |
| 5,200,343 A | 4/1993 | Cole et al. |
| 5,264,018 A | 11/1993 | Koenigsberg et al. |
| 5,277,815 A | 1/1994 | Beeman |
| 5,308,759 A | 5/1994 | Gierhart |
| 5,342,769 A | 8/1994 | Hunter et al. |
| 5,395,419 A | 3/1995 | Farone et al. |
| 5,434,241 A | 7/1995 | Kim et al. |
| 5,464,771 A | 11/1995 | Bryant et al. |
| 5,516,688 A | 5/1996 | Rothmel |
| 5,554,290 A | 9/1996 | Suthersan |
| 5,560,904 A | 10/1996 | Laugier et al. |
| 5,587,317 A | 12/1996 | Odom |
| 5,602,296 A | 2/1997 | Hughes et al. |
| 5,658,795 A | 8/1997 | Kato et al. |
| 5,753,122 A | 5/1998 | Taylor et al. |
| 5,766,929 A | 6/1998 | Orolin et al. |
| 5,833,855 A | 11/1998 | Saunders |
| 5,840,571 A | 11/1998 | Beeman et al. |
| 5,910,245 A | 6/1999 | Bernhardt et al. |
| 5,932,472 A | 8/1999 | Abdullah |

(Continued)

FOREIGN PATENT DOCUMENTS

| EP | 075110981694 | 12/2007 |
| WO | WO 99/24367 | 5/1999 |

(Continued)

OTHER PUBLICATIONS

Callaway, E.S. & Martin, S.A.; "Effects of a *Saccharomyces cerevisiae* Culture on Ruminal Bacteria that Utilize Lactate and Digest Cellulose", Nutrition, Feeding, and Calves; J. Dairy Sci 1997; 80; pp. 2035-2044.

T. Miller-Webster, et al.; "Influence of Yeast Culture on Ruminal Microbial Metabolism in Continuous Culture"; J. Dairy Sci 2002; 85; pp. 2009-2014.

Nisbet, D.J. & Martin, S.A.; "Effect of a *Saccharomyces cerevisiae* culture on lactate utilization by the ruminal bacterium *Selenomonas ruminantium*"; J. Anim. Sci. 1991; 69; pp. 4628-4633.

Rockne, K.J. & Reddy, K.R.; "Bioremediation of Contaminated Sites"; Oct. 2003; International e-Conference on Modern Trends in Foundation Engineering: Geotechnical Challenges and Solutions; pp. 1-22.

(Continued)

*Primary Examiner* — Debbie K Ware
(74) *Attorney, Agent, or Firm* — Lathrop & Gage LLP

(57) ABSTRACT

A method for treating contaminated water or other contaminated media has been developed. Bioremediation enhancing agents (BEAs) such as yeast metabolites (YM) and other yeast derived products are used to facilitate microbial treatment of the contaminated material. Polysaccharides are also an effective BEA when used alone or in combination with the yeast derived products. The BEAs may work with microbes and electron donors to improve the rate of contaminant degradation and to increase the efficiency of electron donor utilization. A number of electron donors are also disclosed.

39 Claims, 12 Drawing Sheets

(56) References Cited

U.S. PATENT DOCUMENTS

| | | | |
|---|---|---|---|
| 5,993,658 | A | 11/1999 | Kato et al. |
| 6,001,252 | A | 12/1999 | Rice et al. |
| 6,039,966 | A | 3/2000 | Kostka et al. |
| 6,264,841 | B1 | 7/2001 | Tudor |
| 6,265,205 | B1 | 7/2001 | Hitchens et al. |
| 6,382,133 | B1 | 5/2002 | Gednalske et al. |
| 6,420,594 | B1 | 7/2002 | Farone et al. |
| 6,472,198 | B1 | 10/2002 | Semprini et al. |
| 6,562,235 | B1 | 5/2003 | Newell et al. |
| 6,589,776 | B1 | 7/2003 | Harkness |
| 6,783,678 | B2 | 8/2004 | Sorenson et al. |
| 7,045,339 | B2 | 5/2006 | Sorenson et al. |
| 7,138,059 | B2 | 11/2006 | Sorenson et al. |
| 7,897,798 | B2 | 3/2011 | McNeff et al. |
| 7,959,806 | B2 * | 6/2011 | Sieczkowski et al. ....... 210/601 |
| 8,057,675 | B2 | 11/2011 | Baseeth et al. |
| 2005/0239189 | A1 | 10/2005 | Schaffner |
| 2006/0000783 | A1 | 1/2006 | Branning et al. |
| 2007/0051676 | A1 | 3/2007 | Chandraghatgi et al. |

FOREIGN PATENT DOCUMENTS

| | | |
|---|---|---|
| WO | WO9966080 | 12/1999 |
| WO | WO0132715 A1 | 5/2001 |

OTHER PUBLICATIONS

Williams, P.E. et al; Effects of the inclusion of yeast culture *Saccharomyces cerevisiae* plus growth medium) in the diet of dairy cows on milk yield and forage degradation and fermentation patterns in the rumen of steers; J. Anim. Sci. 1991; 69; pp. 3016-2036.

Brennan R.A. et al., Biodegradation of Tetrachloroethene by Chitin Fermentation Products in a Continuous Flow Column System Journal of Environmental Engineering, Jun. 2006, pp. 664-673.

Vera, S.M. et al., Evaluation of Different Polymeric Organic Materials for Creating Conditions That Favor Reductive Processes in Groundwater, (2001) Bioremediation Journal 5(3): 169-181.

Passive Remediation of Acid Mine Drainage Using Chitin, Rachel A. Brennan, Mar. 1, 2006, 7 pages.

Daubert, L.N. & Brennan, R.A., A Laboratory Investigation of Passive Acid Mine Drainage Treatment Using Chitin (URE Poster) Apr. 2006, 1 page.

U.S. Appl. No. 12/111,099, Office Action mailed Sep. 17, 2010, 6 pages.

U.S. Appl. No. 12/111,099, Response to Office Action filed Jan. 18, 2011, 12 pages.

U.S. Appl. No. 12/111,099, Notice of Allowance mailed Feb. 4, 2011, 5 pages.

PCT/US2008/061808 International Search Report and Written Opinion, mailed Aug. 7, 2008; 14 pages.

PCT/US2008/ 057250, Invitation to Pay Additional Fees and Partial International Search Report, mailed Jul. 23, 2008; 4 pages.

Laus, R. et al., Reduction of Acidity and Removal of Metal Ions From Coal Mining Effluents Using Chitosan Microspheres, ScienceDirect, Journal of Hazardous Materials, 2007, pp. 471-474.

Moret, A., Rubio, J., Sulphate and Molybdate Ions Uptake by Chitin-Based Shrimp Shells, ScienceDirect, Minerals Engineering, 2003, pp. 715-722.

* cited by examiner

BIOREMEDIATION ENHANCING AGENTS AND METHODS OF USE

RELATED APPLICATIONS

This application claims priority of U.S. Provisional Application No. 60/895,340 filed on Mar. 16, 2007, U.S. Provisional Application No. 60/914,524 filed on Apr. 27, 2007, and U.S. Provisional Application No. 60/972,455 filed on Sep. 14, 2007, and the contents of all three applications are hereby incorporated into this application by reference.

BACKGROUND

1. Field of the Invention

The present disclosure pertains to the use of bacteria in bioremediation of contaminated materials. More particularly, the disclosure relates to the use of certain bioremediation enhancing agents that facilitate degradation of certain chemicals by bacteria.

2. Description of Related Art

The use of carbon substrates as electron donors to enhance reductive dechlorination and the use of oxygen and other oxygen releasing compounds as electron acceptors to enhance the degradation of hydrocarbons have been commercially used to remediate chemical contaminants since at least the early 1990's. A general problem for anaerobic bioremediation of contaminants has been the poor utilization of electron donors. More recently, in order to reduce costs, the industry has moved toward cheaper, less refined substrates with little regard toward substrate efficiency. Some of these lower cost electron donors show poor kinetics and low efficiency. There is therefore a need for improved efficiency of electron donor utilization and enhanced bioremediation kinetics.

Some contaminated sites or contaminated materials contain indigenous microbial communities that are sufficient for complete bioremediation of contaminants. For those sites that are microbiologically limited, addition of nutrients may facilitate the remediation process. Addition of nutrients, such as yeast extract, has been shown to promote the activities of contaminant degrading bacteria in bioremediation of halogenated hydrocarbon contaminated soils. See U.S. Pat. No. 5,766,929. However, no evidence has been reported that such nutrients enhance the efficiency of electron donor utilization in bioremediation. There remains a need for more cost effective nutrients that can enhance the kinetics and/or the efficiency of electron donor utilization in bioremediation.

SUMMARY OF INVENTION

The present disclosure advances the art of bioremediation by providing a method and composition useful in increasing the bioremediation kinetics and enhancing the efficiency of electron donor utilization in a bioremediation process. Nutrients, or Bioremediation Enhancing Agents (BEAs), including yeast products and/or polysaccharides, may be added to a contaminated environment to improve microbial treatment of the contaminated material. The yeast products and polysaccharides may work with microbes and electron donors to improve the rate of degradation of the contaminant. Besides their role in increasing the rates of bioremediation, addition of yeast products and polysaccharides may also increase the efficiency of electron donor utilization. As shown in the examples, addition of yeast products and polysaccharides result in more contaminant being able to be degraded per unit of electron donor consumed.

Yeast products may include, for example, live yeast culture (LYC), yeast metabolites (YM), enzyme-digested yeast (EDY), yeast culture (YC), hydrolyzed yeast (HY), mixed yeast culture (MYC) containing live yeast (LYC), yeast extract (YE), and hydrolyzed yeast (HY), and combination thereof. More preferably, the yeast products to be used are yeast metabolites (YM). Polysaccharides may include but are not limited to beta-glucans, yeast-derived polysaccharides, oligosaccharides, glycans, cellulose, starch, glycogen, chitin, and mixtures thereof. The yeast products and the polysaccharides may be added separately or they may be used in combination. In one embodiment, the polysaccharide to be added is fructooligosaccharide.

The effects of varying amounts of yeast products and polysaccharides have been compared and the suitable range of yeast products and polysaccharide to be used is hereby disclosed. In general, the amount of the bioremediation enhancing agent to be added is an amount that is effective to enhance bioremediation of said contaminated material. In one aspect, this effective amount is equal or greater than the amount sufficient to improve the efficiency of electron donor utilization when compared with a bioremediation reaction without the addition of said bioremediation enhancing agent. In another aspect, the amount of the bioremediation enhancing agent to be added is an amount that is equal or greater than the amount sufficient to increase the kinetics of bioremediation when compared with a bioremediation reaction without the addition of said bioremediation enhancing agent.

More particularly, in one embodiment of the present disclosure, an amount of the bioremediation enhancing agent is effective if it improves by at least 5% the efficiency of electron donor utilization. The improvement of efficiency may be determined by comparing the efficiency of electron donor utilization in different bioremediation reactions with or without the addition of the bioremediation enhancing agent.

In another embodiment of the present disclosure, an amount of the bioremediation enhancing agent is effective if it increases by at least 2% the kinetics of the bioremediation process. The increases of kinetics may be determined by comparing the kinetics of different bioremediation reactions with or without the addition of the bioremediation enhancing agent.

In yet another embodiment, the bioremediation enhancing agent may be added to a contaminated material to achieve a final concentration of about 0.1 mg to about 500 mg of the bioremediation enhancing agent per liter of the bioremediation reaction. For purpose of this disclosure, the volume of a bioremediation reaction is the total volume of the contaminated material after all bioremediation reagents have been added to the contaminated material. Bioremediation reagents may include but are not limited to water or other solvents, BEAs, microorganisms, electron donors or acceptors, and other chemicals that may be beneficial for the bioremediation process.

Certain contaminated materials (or sites) may contain carbon source, such as organic acids that may function as indigenous electron donor. However, under certain circumstances when there is a shortage of electron donors, or when the indigenous electron donor has been exhausted, one or more non-indigenous electron donors may be added to the contaminated materials to facilitate the bioremediation process. For purpose of this disclosure, the electron donors may be selected from the group consisting of a member selected from the group consisting of C2-C6 carboxylic acids and salts or esters or polymers thereof, C2-C6 hydroxy acids and salts or esters or polymers thereof, volatile fatty acids and salts or esters thereof, molasses, sugars, vegetable oil, emulsified vegetable oil substrates, free fatty acids, fatty acid esters, glycerol tripolylactate, HRC®, HRC-X®, HRC Advanced®, (HRC®, HRC-X® and HRC Advanced are Registered Trademarks of Regenesis, Inc.), whey powder, corn syrup, and combination thereof.

In one aspect, a relatively pure preparation containing at least one organic acid may be used as an electron donor. In another aspect, a mixture containing at least one organic acid as well as some residual nutrients and carbohydrates that are left over from the fermentation process that is used to produce the organic acids may be used as an electron donor. By way of example, lactic acid microorganisms may ferment a sugar source such as corn sugar to produce lactic acid. Other compounds may be generated as by-products of the process. The lactic acid may be used together with those by-products to enhance a bioremediation process. It is disclosed here that use of such a mixture may be advantageous over pure form of organic acids. One possible explanation is that the various by-products of the fermentation process may help increasing the bioremediation kinetics as well as enhancing the efficiency of electron donor utilization.

Several novel electron donors for bioremediation and their use are also disclosed. These electron donors include, for example Erythorbate Mother Liquor (ML) (Set B), Lactic Acid Solids (Set D), Crude Glycerol (Set E), Citric Acid and salts thereof (Set E), Gluconic Acid and salts thereof (Set F), Erythorbate and salts thereof (Set F), and polysaccharides (Set G).

One screening test used to correlate reductive dechlorination activity is the production of volatile fatty acids, in particular the ratio of propionate to acetate from the fermentation of an organic substrate in the presence of perchloroethene (PCE).

It is an object of the present invention to provide a method for the enhancement of microbial metabolic kinetics and efficiencies of both indigenous and non-indigenous microbial populations through the addition of yeast products and/or polysaccharides.

It is also an object of this invention that the process be used to enhance the metabolic kinetics and efficiencies of indigenous and non-indigenous microbial populations specific to the in situ and ex situ remediation of soil, groundwater, or a combination of both soil and ground water, containing organic contaminants, inorganic contaminants, or a combination of both organic and inorganic contaminants utilizing either aerobic or anaerobic metabolic pathways or both.

It is also an object of this invention that the process be used to enhance the metabolic kinetics and efficiencies of indigenous and non-indigenous microbial populations specific to the degradation of organic, inorganic, or a combination of both organic and inorganic substances in waste water and storm water contained in process equipment or within containment structures associated with publicly-owned treatment plants (POTW's) or privately-owned waste water or storm water treatment systems. It is also an object of this invention that the process be used to enhance the metabolic kinetics and efficiencies of microorganisms within or on other organisms to change the physical or chemical state of organic or inorganic substances.

It is further an object of this invention that the process be used through direct surface application of yeast products and polysaccharides, mixing of yeast products and polysaccharides with electron donor substrates, nutrients, or organisms, or through the passive introduction of yeast products and polysaccharides into the environment.

Another object of this invention is that certain contaminated materials (or sites) may be bioremediated more quickly or efficiently using an aerobic process wherein the contaminant may be bioremediated through an oxidative biodegradation process. See e.g., Rockne and Reddy, BIOREMEDIATION OF CONTAMINATED SITES, International e-Conference on Modern Trends in Foundation Engineering: Geotechnical Challenges and Solutions, Indian Institute of Technology, Madras, India, (October 2003). In one aspect, the contaminant may itself act as the electron donor and the contaminated materials (or sites) may contain oxygen or other electron acceptors such as nitrate or sulfate that may function as indigenous electron acceptors. However, under certain circumstances when there is a shortage of electron acceptors, or when the indigenous electron acceptor has been exhausted, one or more non-indigenous electron acceptors may be added to the contaminated materials to facilitate the bioremediation process. Examples of electron acceptors may include but are not limited to oxygen, sulfate, nitrate, peroxide, oxidizing agents, permanganates, ozone, compounds that chemically or biologically generate oxygen, metallic peroxygens, ORC®, ORC-Advanced®, RegenOx™ (ORC®, ORC-Advanced®, RegenOx™ are Trademarks of Regensis, Inc.), or mixtures thereof. BEAs added to these preferentially aerobic bioremediation systems may improve the rate of bioremediation of the contaminant or may increase the efficiency of utilization of the electron acceptor for bioremediation or both.

Some contaminants that may be bioremediated through an aerobic pathway may include but are not limited to petroleum hydrocarbons, aliphatic and aromatic hydrocarbons such as BETX compounds, gasoline, and diesel fuel. In addition, PCB, pesticides, dioxins and certain metals may be also aerobically bioremediated.

In another aspect, certain bioremediation processes may generate significant amount of energy in the form of thermal or chemical energy. Under certain circumstances, it may be desirable to capture some or all of these various forms of energy or to convert them into energy forms that can be more readily used.

DETAILED DESCRIPTION

Figure 1:
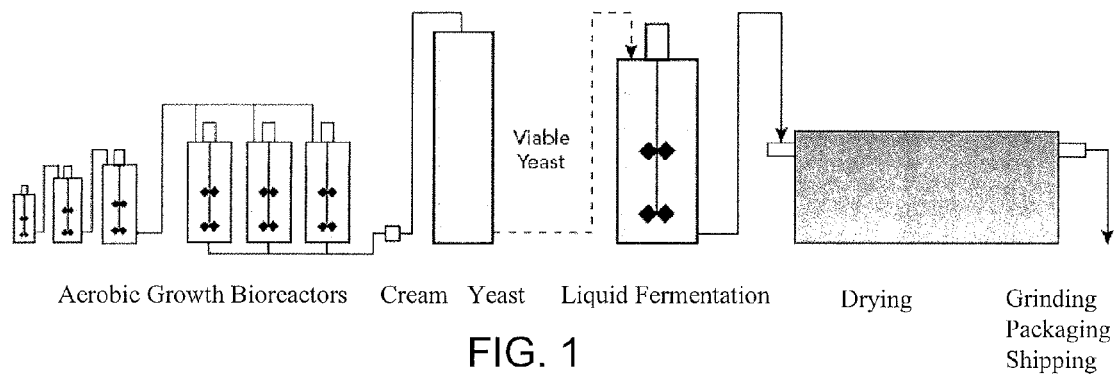
FIG. 1 illustrates schematically a representative procedure to produce yeast metabolites (YM).

This disclosure provides an improved method for enhancing the efficiency and kinetics of bioremediation of a contaminated material. The term "contaminated material" may refer to any sites, media or objects that have been contaminated by chemicals as a consequence of human activities or natural causes. Applicable contaminant materials may include but are not limited to water, other liquid, solid or gaseous media or media of other phases or mixed phases that contain chemicals potentially harmful for human, animal or the environment in general.

The disclosed method may be applicable to contaminated material containing either halogen-containing chemicals or non-halogen-containing chemicals. Halogen-containing chemicals may include but are not limited to halogenated aliphatic hydrocarbon and halogenated aromatic hydrocarbon. Non-halogen-containing chemicals may include but are not limited to aliphatic hydrocarbon and aromatic hydrocarbon, such as benzene, toluene, ethylbenzene, and xylene (BTEX). In another aspect, chemicals suitable to be treated by the bioremediation methods disclosed herein may also include but are not limited to perchlorate salts, pesticides, metals, nitrates, sulfates, MTBE, industrial or municipal waste water, polychlorinated biphenyls (PCBs), Acid Mine Drainage (AMD), radio nucleotides and dioxins.

In one aspect, the methods disclosed herein may be useful for enrichment and/or conversion of certain chemicals present in a contaminated material (or site). For instance, the composition disclosed may enhance the growth and metabolism of certain microbes which selectively transport chemicals into their cells. Some microbes may store the chemicals; others may convert the chemicals into different chemicals. Sometimes, it may be advantageous to employ microbes that simply store the chemicals so that the chemicals may be enriched and harvested later. Under other circumstances, it may be more desirable to employ microbes that convert one chemical into another chemical that is less harmful, or sometimes, more valuable.

The specification sheets of various commercially available products are shown in this disclosure. It is recognized that these Spec Sheets are shown for purpose of illustration only. It is understood that certain physical or chemical properties of the products may be modified without departing from the spirit of the present disclosure. One of ordinary skill in the art may appreciate that under certain circumstances, it may be more desirable or more convenient to alter certain physical and/or chemical characteristics of one or more of these components in order to achieve the same or similar objectives as taught by this disclosure.

It is to be noted that, as used in this specification and the claims, the singular forms "a," "an," and "the" include plural referents unless the context clearly dictates otherwise. Thus, for example, reference to "an electron donor" includes reference to a mixture of two or more of such electron donors, reference to "a solvent" includes reference to one or more of such solvents, and reference to "a microbe" includes reference to a mixture of two or more of such microbes. Unless otherwise specified, terms with all or some letters capitalized may be used interchangeably with terms with lower case letters.

Inoculum

Certain contaminated materials (or sites) may contain indigenous microbial communities that are sufficient for complete bioremediation of contaminants. For such sites, there is no need to add microbes unless the indigenous microbes are genetically deficient in achieving the desired clean-up goals. For those sites that are microbiologically limited, microorganisms may be added to the contaminated materials (or sites). In one embodiment, the inoculum may be a mixed culture of halo-respiring bacteria that have been enriched to reach an optimal cell density. These mixed cultures of halo-respiring bacteria may be typically obtained from sediment samples from rivers, streams or any waterways. More specifically, the inoculum used in the Examples was originated from a Sangamon River sediment sample (Lodge Park, Piatt County, Ill.) See, e.g., Brennan, R. A., Sanford, R. A. and Werth, C. J. (2006). "Biodegradation of Tetrachloroethene by Chitin Fermentation Products in a Continuous Flow Column System." *Journal of Environ. Engr.*, June 665-673. This culture had grown for several years on PCE, anaerobic basal salts medium, Wolfe's vitamin solution and various electron donors including lactate (1-2 millimolar (mM)), formate (4 mM) and chitin using the Volatile Interface Transfer Apparatus (VITA) reactor system at the University of Illinois. Brennan, R. A., and Sanford, R. A. (2002). "Continuous steady-state method using Tenax for delivering tetrachloroethene to chlororespiring bacteria." *Appl. Environ. Microbiol.*, 68(3), 1464-1467. In 2003, microscopic direct count estimates showed that the culture's density exceeded $1 \times 10^9$ cells/ml. Using 16S rRNA gene-specific primers, both *Dehalococcoides* and *Dehalobacter* spp. were detected. Quantitative real-time PCR has been used to determine that approximately $1.65 \times 10^7$ *Dehalococcoides* gene copies were present per ml of culture.

Nutrient Description

Various nutrients, including yeast derived products (or yeast products) and polysaccharides, are shown here to enhance bioremediation of a variety of contaminated materials. The terms "nutrient" and "bioremediation enhancing agent" may be used interchangeably in this disclosure. "Carbohydrate" may include polysaccharides, oligosaccharides, and monosaccharide and their derivatives. Yeast derived products may be further classified into the following categories: live yeast culture (LYC); yeast extract (YE); yeast metabolites (YM); enzyme-digested yeast (EDY); yeast culture (YC); hydrolyzed yeast (HY); and mixed yeast culture (MYC) containing live yeast (LYC), yeast extract (YE), and hydrolyzed yeast (HY).

"Live yeast culture" (LYC), also referred to as "live yeast" (LY) may be described as living or temporarily dormant yeast cells typically from cultures of *Saccharomyces cerevisiae* or other species of budding or fission yeast. The yeast may be mixed with grain products such as ground yellow corn, corn gluten meal, condensed fermented corn extract, cane molasses, or malted barley. Examples of live yeast culture or live yeast may include but are not limited to various materials produced by Western Yeast Company, Inc. of Chillicothe, Ill. By way of example, one such live yeast is CEL-CON 5 (LYC1) produced by Western Yeast Company. The product specification sheet of LYC1 is shown below for purpose of illustration:

| TYPICAL ANALYSIS: | |
|---|---|
| Crude Protein | >18% |
| Crude Fat | >3% |
| Crude Fiber | >5% |

Other LYCs based on other strains of *Saccharomyces cerevisiae* may also be used. For instance, LYC2 is a dried form of *Saccharomyces cerevisiae* strain 1026. A modified form of LYC2 in a more concentrated form is also tested in this disclosure and is referred to as LYC3. LYC3 contains about twice the concentration of *Saccharomyces cerevisiae* strain 1026 as LYC2.

As is commonly known in the art, Yeast Extract (YE) is a water soluble extract of autolyzed yeast cells. Yeast extract is a mixture of amino acids, peptides, water soluble vitamins and carbohydrates and can be used as additive for culture media. Examples of "yeast extract" may include but are not limited to various products sold by Sigma in the form of BioChemika, microbiology grade (YE1). The Spec Sheet of YE1 is listed below for purpose of illustration:

| TYPICAL PROPERTIES: | |
|---|---|
| Appearance | Clear yellow |
| pH (2% in Water) | 6.8-7.2 |
| Solubility | 2% |
| Total nitrogen | 11% |
| Amino nitrogen | 0.5% |
| Ignition Residue | 15% |
| Loss on Drying | 6% |

For purpose of this disclosure, the singular form and plural form of the term yeast metabolite(s) (YM) may be used interchangeably to describe one or more metabolites (or nutrients) produced by yeast cells that have been grown for at least 15 minutes under anaerobic conditions. When a population of yeast cells are said to be grown under "anaerobic conditions," it means that more than 90% of the cells do not have continuous supply of oxygen for at least 15 minutes while they are still alive. It is to be recognized that although yeast cells grown under aerobic conditions also produce metabolites, the YM as disclosed here contains metabolites that are produced by the yeast cells under anaerobic conditions. For purpose of enhancing bioremediation, the various forms of YM disclosed herein are preferable over other products, such as yeast extract (YE) that may contain yeast metabolites produced under aerobic conditions. Products such as YE that may contain yeast metabolites produced by yeast cells grown under aerobic but not anaerobic conditions are not within the meaning of YM for purpose of this disclosure.

In a preferred embodiment, YM is prepared from yeast cells, along with their culture media, that have been incubated for a period of at least 30 minutes under anaerobic conditions. It is hereby disclosed that YM may contain a broad range of molecules that are beneficial to the proliferation and/or metabolism of microbes in a bioremediation process. Examples of such beneficial molecules may include vitamins, minerals, amino acids, antioxidants, nucleic acids, fatty acids, peptides, etc, that are produced by yeast cells under anaerobic conditions.

In one aspect, sugar sources such as corn syrup and cane molasses may be fermented utilizing a multi-step fermentation and drying process to produce the YM, as illustrated in FIG. 1. More specifically, YM may be produced by first propagating yeast in a wort that may contain sugars, starches, enzymes and proteins under aerobic conditions. When the yeast cells are in the exponential growth phase after an initial aerobic growth period, they are shifted to an anaerobic condition. A mix of nutrients may be added at this stage to the culture medium. The wort may be allowed to ferment anaerobically between 50° F. and 80° F. This period is also known as the first fermentation. The duration of this period is preferably at least 30 minutes, and more preferably ranging from 1 hour to as long as 90 days. Under this anaerobic environment, the yeast cells are stressed which may cause them to produce specific metabolites under anaerobic conditions.

The liquid fermentation phase may contain multiple steps of fermentation (not shown in FIG. 1). At the end of the fermentation phase, the yeast culture including the cells and the culture medium may be dried to concentrate the array of nutrients and metabolites in the medium to produce YM1.

A modified form of YM may be produced by adding to the broth of YM1 various supplements prior to its dehydration. Examples of these supplements may include ground yellow corn, hominy feed, corn gluten feed, wheat middlings, rye middlings, diastatic malt and corn syrup, cane molasses, other starches or carbohydrates or mixtures thereof in an amount or manner to form a dough. This dough may be extruded, dried, and ground forming YM2. YM3 may be produced in a similar fashion to YM2 except preparation of YM3 starts with higher concentrations of YM in the YM1 broth. YM4 is a more finely ground version of YM3.

The YM products thus prepared may contain yeast proteins, various biological factors, vitamins and mixtures of metabolites generated by fermenting yeast under anaerobic conditions. The fermentation and drying processes are preferably conducted under mild conditions such that the yeast proteins, factors, vitamins and other fermentation products are not destroyed.

Suitable fermenting yeast includes, for example, *Saccharomyces cerevisiae*. Other yeast strains capable of fermentation may also be used. Selection and manipulation of yeast may be performed according to C. Guthrie and G. R. Fink, Guide to Yeast Genetics and Molecular Biology (Methods in Enzymology, Vol. 194), Academic Press (February 1991).

Examples of yeast metabolites (YM) may include but are not limited to various products produced by Embria Health Sciences, L.L.C. of Ankeny, Iowa. The Physical and Chemical Properties listed on the spec sheet of EpiCore® High-Metabolite Immunogens (YM1) are shown below for purpose of illustration:

| TYPICAL ANALYSIS: | |
| --- | --- |
| Moisture | <11% |
| Protein | >25% |
| Ash | <20% |
| Fat | >0.1% |
| Total Dietary Fiber | >10% |
| ORAC Value | 450-650 |
| MICROBIOLOGY: | |
| Aerobic Plate Count | <100,000 cfu/g |
| Yeasts & Mold | <1,000 cfu/g |
| Total Coliforms | n.d.* |
| Staph. Aureus | n.d.* |
| Pseudomonas aeruginosa | n.d.* |
| Salmonella sp. | Negative |
| HEAVY METALS: | |
| Arsenic (As) | <1 mcg/g |
| Cadmium (Cd) | <1 mcg/g |
| Lead (Pb) | <1 mcg/g |
| Mercury (Hg) | <1 mcg/g |

Enzyme digested yeast (EDY) refers to the product of an enzymatic breakdown of the cells of the yeast Saccharomyces cerevisiae grown in a specific medium. Examples of "enzyme digested yeast" may include but are not limited to various products produced by Varied Industries Corporation of Mason City, Iowa. A preferred form of enzyme digested yeast is Celmanax® Liquid (EDY1), the Spec Sheet of which is shown below for purpose of illustration:

| TYPICAL ANALYSIS: | |
| --- | --- |
| Moisture | 80% |
| Dry Matter | 20% |
| Crude Protein | 6% |
| Crude Fat | 1.6% |
| Crude Fiber | 2.2% |
| Ash | 0.8% |

Yeast Culture (YC) refers to yeast cells, such as cells of Saccharomyces cerevisiae, together with the media on which they grow. Typical media may contain, for example, glucose, sucrose, cane sugar, cane molasses and corn syrup, or processed grain products. Examples of "yeast culture" may include but are not limited to various products produced by Varied Industries Corporation of Mason City, Iowa. A particular line of product in the form of A-MAX® Yeast Culture ULTRA (YC1) is used in this disclosure. The Spec Sheet of YC1 is shown below for purpose of illustration:

| TYPICAL ANALYSIS: | |
| --- | --- |
| Moisture | <10% |
| Dry Matter | 90% |
| Crude Protein | >23% |
| Crude Fat | >3% |
| Crude Fiber | >10% |
| Ash | <3% |
| Total Digestible Nutrients | >74% |

For purpose of this disclosure, mixed yeast culture (MYC) containing LYC, YE, and hydrolyzed yeast (HY) generally refer to a preparation of various yeast components derived from the fermentation of a specific culture containing cells of Saccharomyces cerevisiae or other species of budding or fission yeast. The term "hydrolyzed yeast" (HY) refers to yeast extract that is chemically degraded through hydrolysis. Examples of MYC may include but are not limited to various products produced by Varied Industries Corporation of Mason City, Iowa, such as the product Celmanax® Yeast Culture, Yeast Extract, and Hydrolyzed Yeast (MYC1) that is used in this disclosure. The Spec Sheet of MYC1 is shown below for purpose of illustration:

| TYPICAL ANALYSIS: | |
| --- | --- |
| Moisture | 10% |
| Dry Matter | 90% |
| Crude Protein | 23% |
| Crude Fat | 3.6% |
| Crude Fiber | 8.4% |
| Ash | 3% |
| Total Digestible Nutrients | 74.3% |

Polysaccharide (PS) generally refers to a carbohydrate polymer made up of two or more molecules of monosaccharides. Examples of polysaccharides suitable for purpose of this disclosure may include but are not limited to oligosaccharides, beta-glucan, glycans, cellulose, starch, glycogen, chitin, or mixtures thereof. One type of polysaccharide is the class of fibers known as fructans. Inulin, which is one type of fructooligosaccharide (FOS) commonly used as a water-soluble dietary fiber, is used in this disclosure to evaluate the effects of polysaccharide on the bioremediation process. Inulin is extracted from Jerusalem Artichoke tubers in pure form and is found naturally in more than 36,000 types of plants worldwide. Inulin is a natural polymer containing fructose units generally terminating in a glucose unit. More particularly, the inulin used in this disclosure is produced by Becwood Technology Group, L.L.C. of Independence, Minn. and sold under the name ULTRA-FOS® (PS1). The Spec Sheet of PS1 is shown below for purpose of illustration:

| TYPICAL ANALYSIS: | |
| --- | --- |
| Moisture | <10% |
| Dry Matter | >95% |
| Carbohydrate Content | >99% |
| Inulin | >90% |
| Mono & disaccharides | <10% |
| Ash | <1% |
| Average Chain Length | 7-12 |
| Appearance | White Powder |
| Dispersibility in water | Good |
| Behavior | Free Flowing |
| pH (10% solution) | 4.5-7.0 |

In another aspect, polysaccharides in the form of oligosaccharides in less pure form derived from certain yeast cells may be used as polysaccharide, and is sometimes referred to as "yeast derived polysaccharides" in this disclosure. One specific form of such oligosaccharides designated PS2 is tested in this disclosure.

Bioremediation Microcosms

In order to assess the effect of the BEAs on bioremediation, the reactions may be carried out with or without the BEAs and the results are measured. The BEAs and the electron donors maybe added into a bioremediation mix in any physical forms, preferably in either liquid or solid form. The amount of the bioremediation enhancing agent to be added to the reaction may be determined by measuring the kinetics and the efficiency of electron donor utilization in the presence or absence of the BEAs in a pilot experiment. For purpose of this disclosure, "an amount sufficient to improve the efficiency of electron donor utilization" means an amount of a substance that will positively affect the efficiency of electron donor utilization when such a substance is added in such an amount to a reaction. Similarly, "an amount sufficient to increase the kinetics of bioremediation" means an amount of a substance that will positively affect the kinetics of bioremediation when such a substance is added in such an amount to a reaction.

For purpose of this disclosure, each bottle may be started with a certain amount of PCE. At subsequent times each bottle may be sampled for the degradation daughter products of PCE, namely trichloroethene (TCE), cis-dichloroethene (DCE), vinyl chloride (VC) and ethene, etc. Trans-DCE and 1,1-DCE are also daughter products of PCE, but they may not be detectable under the conditions disclosed here.

The rate of degradation may be determined by calculating the number of µmoles of chloride ions removed from PCE and subsequently from the amounts of the daughter products generated. The calculation may be performed as follows:

$$Chloride(\mu moles)=Starting\ PCE(\mu moles)-4\times PCE(\mu moles)-3\times TCE(\mu moles)-2\times DCE(\mu moles)-VC(\mu moles)$$

An alternative calculation may be used for low activity sets that do not generate many daughter products or sets where the uninoculated control shows loss of PCE. The alternative chloride calculation is:

$$Chloride(\mu moles)=TCE(\mu moles)+2\times DCE(\mu moles)+3\times VC(\mu moles)+4\times Ethene(\mu moles)$$

Next, the dechlorination rate may be determined for each bottle at each time by dividing the Chloride generated by the time (days). The data may be then normalized to the lactate control by taking the ratio of Chloride Rate (µmoles/day) and the Lactate Control Chloride Rate (µmoles/day). This ratio is called Relative Rate and is dimensionless.

As shown in the Examples, a paired t-test has been conducted to calculate the probability that the Relative Rate of one group (i.e. with Nutrient) is greater than the other group (i.e. without Nutrient). The null hypothesis is that the underlying means of the two paired groups are equal. The Probability that one group has higher Relative Rates than the other group is shown in various tables in the Examples.

The Examples below also contain figures showing the relative amount of dechlorination daughter products remaining at the sampling points near the end of each experiment. A bioremediation amendment showing ethene generation at this stage may be considered to have successfully demonstrated its ability to be an electron donor for the bioremediation of contaminants in water, or other sources.

Sets B, C, D, E, and G further contain figures and tables showing results of the characterization of the Efficiency and the Relative Efficiency of electron donor usage. Efficiency may be defined as the percent of electron donor utilized for dechlorination, and may be calculated by dividing the µmoles of Chloride ion generated by the µmoles of electron donor consumed as measured by either Volatile Fatty Acid (VFA) analysis (Sets B, C, and G) or Chemical Oxygen Demand (COD) analysis (Set D and E). The Relative Efficiency of the electron donor utilization may be defined as the Efficiency of the Electron Donor divided by the Efficiency of the Lactate Control.

In another aspect, a mixture of at least one organic acid may be used as electron donor. It is also provided here that such a mixture may also contain nutrients and/or carbohydrates residual from a fermentation process that is used to produce at least one of the organic acids. Examples of such organic acids include but are not limited to carboxylic acids, hydroxyl acids or volatile fatty acids or their salts or esters, such as lactic, acetic, fumaric, propionic, butyric, succinic acids.

Thus, all of the Bioremediation Enhancing Agents (BEAs), including both the yeast derived products and the polysaccharides, increase fermentation rates and, where tested, increased the kinetics and efficiencies of electron donor utilization.

In the case of the VFA screening test, all BEAs tested improved the lactate fermentation rates. The Yeast Metabolites, Mixed Yeast Culture and Polysaccharides gave superior results for propionate to acetate molar ratios. The Live Yeast Cultures improved over time and given more time, all three Live Yeast Cultures would likely have also generated better propionate to acetate ratios as compared to lactate. By day 11, two of the three Live Yeast Cultures did outperform the lactate control. It is possible that the Live Yeast Cultures were generating anaerobic yeast metabolites over time in-situ. In Set G, the Yeast Metabolites outperformed the Polysaccharides on contaminant degradation rates and on the efficiency of electron donor utilization. Set C shows that Yeast Metabolites outperformed Yeast Extracts and a proprietary Vitamin mix. The superior Yeast Metabolites performance as compared to the other commercially available nutrients is especially significant because the usage rate for the YM is much lower than the Yeast Extract and the Vitamin mix. Based on the results of the screening test, Yeast Metabolites as a class of compounds are the most preferred BEAs as compared to all the other BEAs tested.

As disclosed here, the Yeast Metabolites in the form of 1% YM2, 10% YM2 and YM1 all demonstrate superior metabolic kinetics and efficiency in these microcosms. YM2 nutrient may be supplemented from about 0.1% to about 20%. Higher than 20% Nutrient may be used but the total cost will be significantly higher. The beneficial effects of YM and other yeast products and polysaccharides may apply to other electron donors as well. Thus, the disclosed methodology may be applied to improving bioremediation of both anaerobic as well as aerobic processes in water and extend from in-situ treatment of contaminated ground water to surface and or process waters.

All seven of the novel electron donors for bioremediation, namely, Erythorbate Mother Liquor (ML) (Set B), Lactic Acid Solids (Set D), Crude Glycerol (Set E), Citric Acid and salts thereof (Set E), Gluconic Acid and salts thereof (Set F), Erythorbate and salts thereof (Set F) and Polysaccharides (Set G) show the capacity to dechlorinate PCE all the way to ethene, with the caveat that all seven appear to be slower and less efficient than lactate in facilitating the bioremediation process as described herein. Molasses also demonstrates the capacity to dechlorinate PCE all the way to ethene, albeit slower and less efficient than lactate.

EXAMPLES

The following examples illustrate the present invention. These examples are provided for purposes of illustration only and are not intended to be limiting. The chemicals and other ingredients are presented as typical components or reactants, and various modifications may be derived in view of the foregoing disclosure within the scope of the invention.

All Bioremediation Microcosms described in the Examples contain the components that are in the size suitable for a laboratory setting. It is important to note that these small scale experiments disclosed herein may be scaled up and the principle of operation and the proportion of each component in the system may equally apply to a large-scale bioremediation system. Each specific formulation was run in triplicate and each bottle was sampled for PCE and daughter products at several different times during the PCE degradation. The number of points and times of the sampling were selected to be able to monitor the reduction in PCE and the subsequent increase and then degradation of the daughter products. Unless otherwise specified, the percentages of components used in this disclosure are on a w/w basis.

Example 1

VFA Screening Test

Volatile Fatty Acid (VFA) generation microcosm tests were used to characterize the rate of propionate generation, the absolute level of propionate generation and the molar ratio of propionate to acetate, a proxy for electron donor efficiency. The triplicate bottles were sampled five times over the first 11 days of the test.

The screening test evaluated the fermentation of sodium lactate amended with various yeast products and polysaccharides (bioremediation nutrients) in the presence of PCE. The nutrient amended lactate may be prepared by adding 3.9 g of bioremediation nutrient to 250 ml of sodium lactate 60% solution. The following bioremediation nutrients were evaluated in the screening tests:

Live Yeast Cultures: LYC1, LYC2 and LYC3

Yeast Culture: YC1

Mixed Yeast Culture: MYC1

Yeast Metabolites: YM3

Enzyme Digested Yeast: EDY1

Polysaccharide: PS2

The following components were used in the system for the VFA Screening Test:

160 milliliter (ml) stoppered serum bottles 100 ml of anaerobic culture medium, groundwater containing an excess of bioavailable phosphorus and nitrogen at 0.5 mM Phosphate and 1 mM ammonium degassed with a nitrogen sparge 2 microliters (μl) perchloroethene (PCE)

11 mM lactate 2 ml of inoculum containing dechlorinating bacteria known to convert PCE to ethene.

Figure 2:
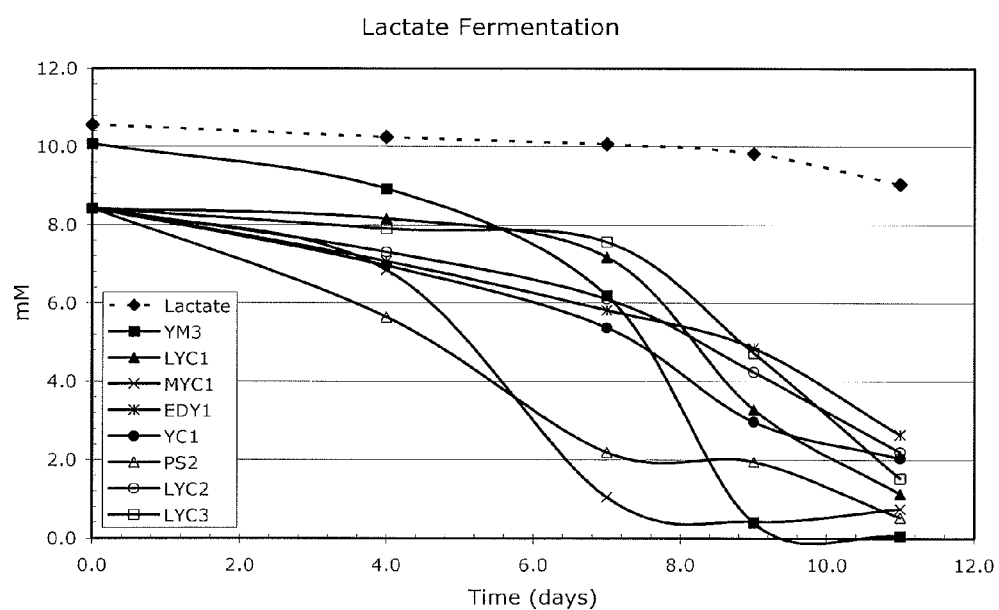
FIG. 2 shows the fermentation of lactate over time for various yeast products and polysaccharides.

The fermentation rate of the lactate of all eight of the bioremediation nutrients out-performed that of lactate as shown in FIG. 2. Both the PS2 and the MYC1 fermented the lactate rapidly by the seventh day, but the fermentation rates of both PS2 and MYC1 slowed considerably by the eleventh day and were overtaken by YM3 on the ninth day. By the eleventh day only YM3 facilitated the complete fermentation of the lactate. The lactate fermentation with the MYC1 appeared to have completely stopped by the ninth day.

Figure 3:
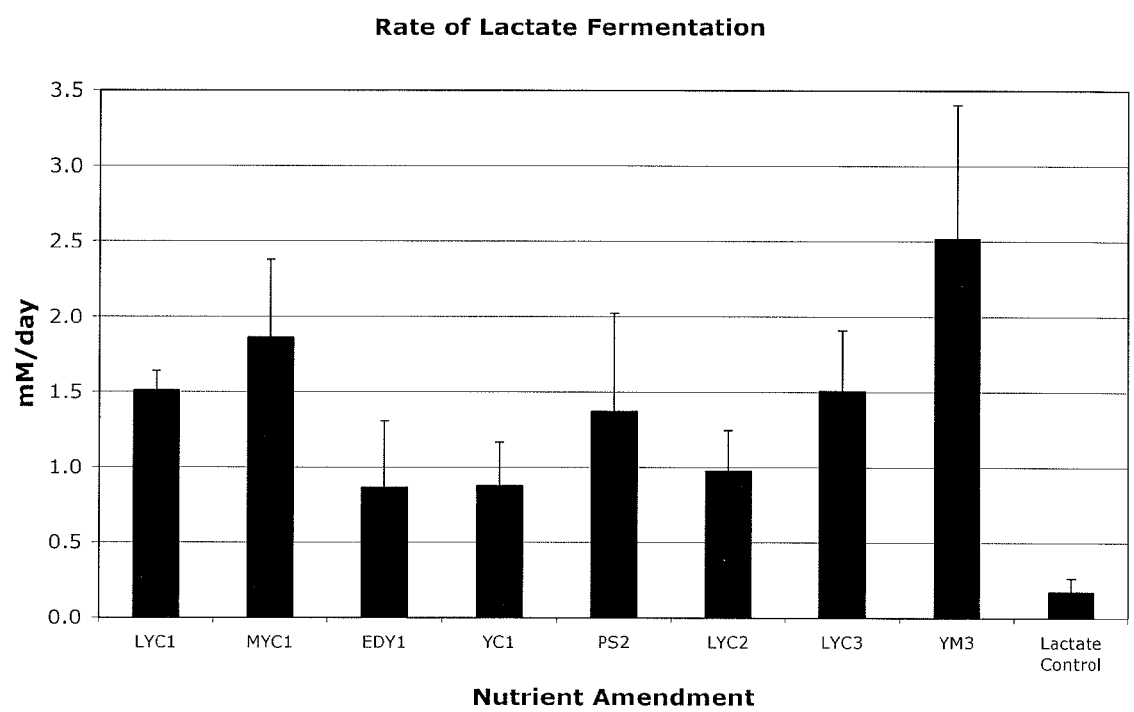
FIG. 3 compares the maximum rate of lactate fermentation of various yeast products and polysaccharides.

Using the maximum lactate fermentation rate as shown in FIG. 3, the YM3 had the highest rate followed by MYC1 and PS2. The error bars indicate the standard deviation of the result among the triplicates. The three live yeast cultures started out the slowest and then began to catch up to the other bottles by the eleventh day. This observation suggests that the metabolites being produced by the live yeast culture in situ might help enhance the fermentation rate of the lactate.

The EDY1 and the YC1 fermented lactate the slowest.

Figure 4:
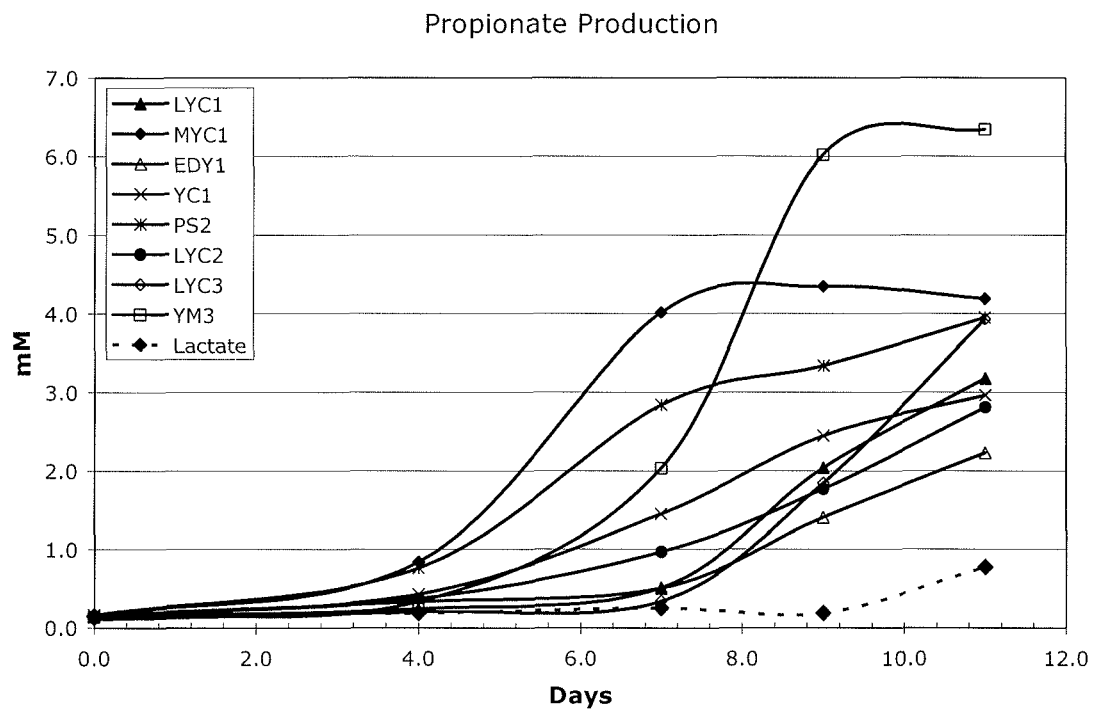
FIG. 4 shows the production of propionate for various yeast products and polysaccharides.

The propionate generation shown in FIG. 4 parallels the lactate fermentation rate results in that the increase in propionate level correlates with the decrease in the level of the lactate.

Again the YM3, MCY1 and PS2 generated propionate the fastest, but the other 5 nutrients started generating significant amounts of propionate by the eleventh day with the live yeast cultures generating most of their propionate after the seventh day.

Figure 5:
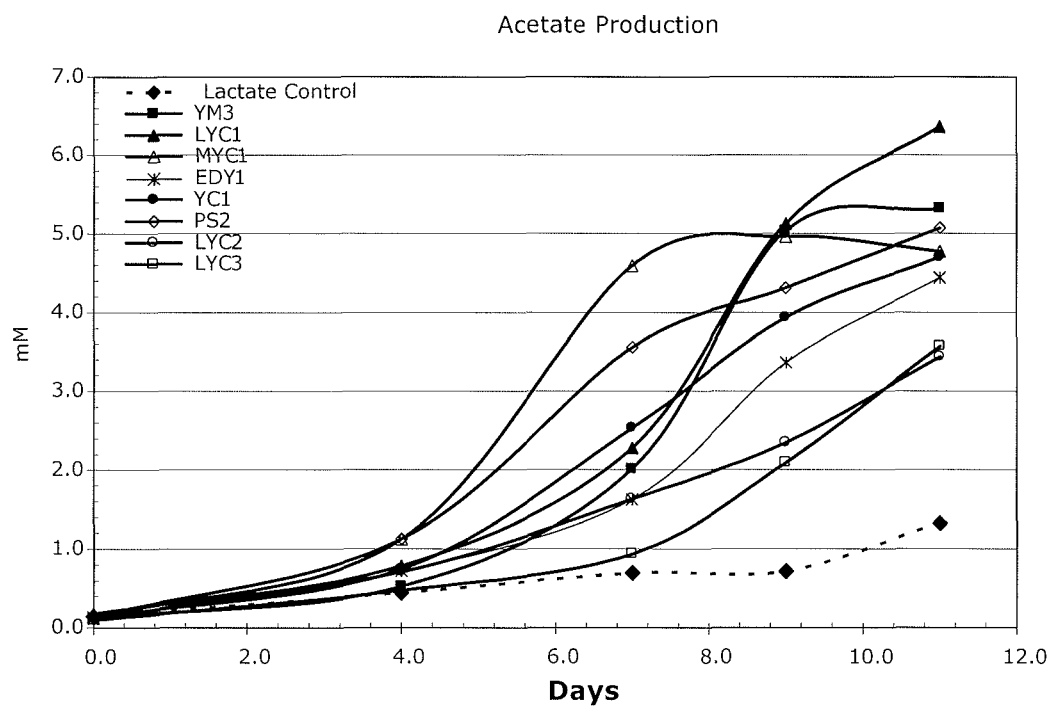
FIG. 5 shows the production of acetate for various yeast products and polysaccharides.

The acetate generation shown in FIG. 5 parallels the lactate fermentation rate results in that the appearance of acetate correlates with the disappearance of the lactate with the exception of LYC1 which generated the most acetate.

Again the YM3, MCY1 and PS2 generated acetate the fastest, but the other 5 nutrients started generating significant amounts of acetate by the eleventh day with the live yeast cultures generating most of their acetate after the seventh day. LYC1 generated the most acetate by the eleventh day.

Figure 6:
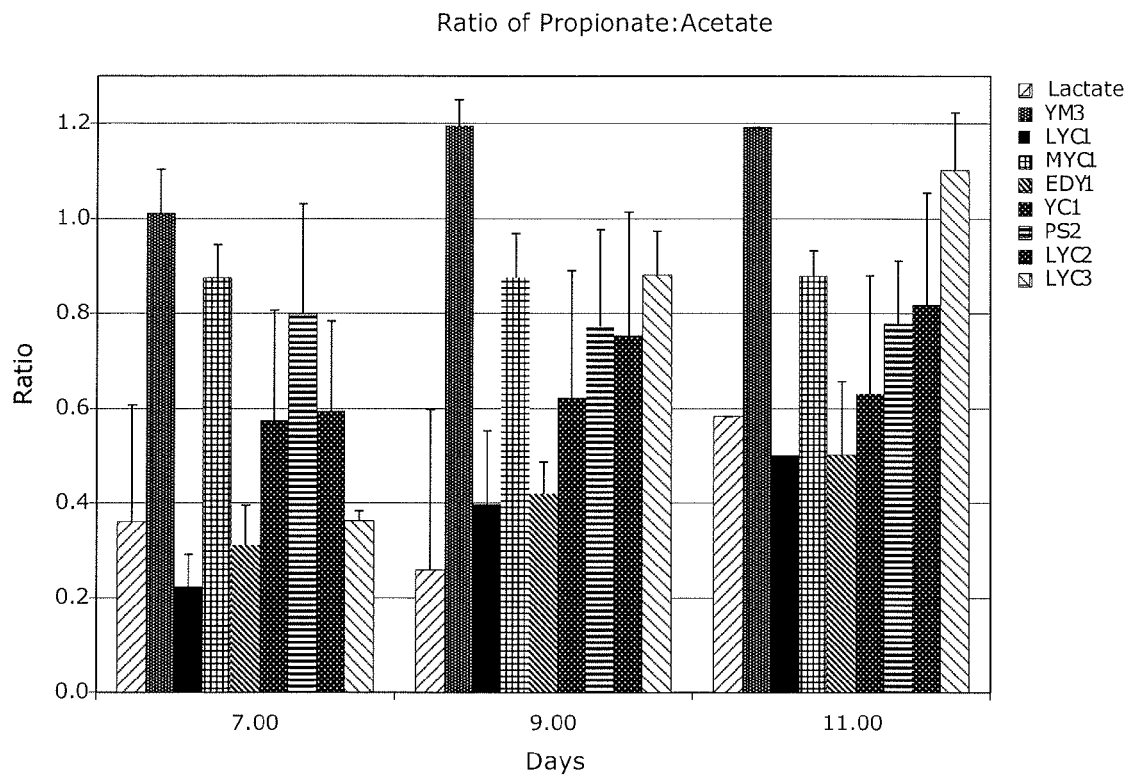
FIG. 6 shows the mean molar ratio of propionate to acetate at the 7, 9 and 11 day point for various yeast products and polysaccharides.

The ratio of propionate to acetate generation may be a proxy for how efficiently the microorganisms will utilize the electron donor for dehalogenation processes. In this case, FIG. 6 shows that at all three time points, the Yeast Metabolite product (YM3) had the highest ratio, although Live Yeast Culture (LYC3) which started out very low and statistically no different from the control at 7 days, by 11 days was statistically the same as the YM3. The ratio of all three Live Yeast Cultures (LYC1, LYC2, LYC3) increased over time. The ratios of the remaining non-live samples including the lactate control remained invariant. The live yeast cultures may be generating beneficial yeast metabolites in-situ and thus providing a similar benefit to the propionate to acetate ratio as the yeast metabolite products. The performance of the live yeast culture appear to be concentration dependent as the LYC3 has twice the live cell count as LYC2.

Example 2

Set A: Ladder of YM

The following components were used in the system for bioremediating contaminated ground water microcosms in Examples 2-8:

160 milliliter (ml) stoppered serum bottles 100 ml of anaerobic culture medium, groundwater containing an excess of bioavailable phosphorus and nitrogen at 0.5 mM Phosphate and 1 mM ammonium degassed with a nitrogen sparge Nominally 1 gram of limestone 19.54 micromoles (μmoles) Perchloroethene (PCE)

An excess of various electron donors were utilized 3 ml of inoculum containing dechlorinating bacteria known to convert PCE to ethene.

The first set of microcosms used sodium lactate as the electron donor at 7 mM in all the bottles. The four replicates were as follows:

1% YM2

10% YM2

Lactate control—No YM

No Lactate and 100 mg of YM2

Figure 7:
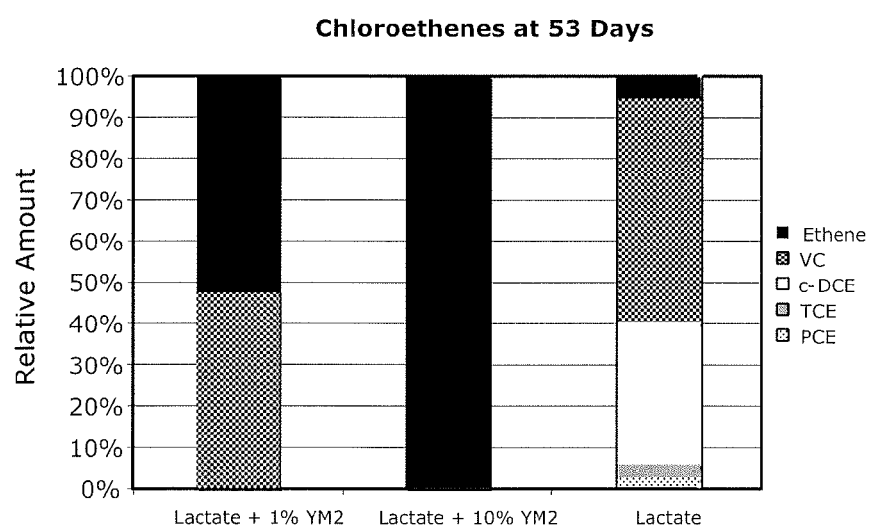
FIG. 7 shows the degradation of PCE to ethene when adding both 1% and 10% YM2 nutrient to the microcosm.

The objective of this set was to characterize the improvement in kinetics from adding different levels of the YM2. The No Lactate bottles were used to determine if the YM2 on matrix alone could also be utilized as electron donor. In the case of the yeast metabolite, the yeast metabolite may be added according to the following procedure. One gram (1% YM2) or 10 grams (10% YM2) is added to 100 ml of water, agitated and allowed to come to equilibrium, then 1 ml of the resulting solution is added to the microcosm. In the case of nutrients in powder form, the powder may be added to the microcosms directly. FIG. 7 shows the rapid degradation of PCE to ethene when adding both 1% and 10% YM2 to the microcosm.

Tables 1-4 show the kinetic results, and include concentrations of PCE and its daughter products, Chloride generation ($Cl^-$) and Chloride Rate ($Cl^-$ Rate) and the associated standard deviation (s.d.) of results from the three bottle triplicates.

TABLE 1

Lactate + 1% YM2

| Time (days) | PCE ± s.d. (µmoles) | TCE ± s.d. (µmoles) | DCE ± s.d. (µmoles) | VC ± s.d. (µmoles) | Ethene ± s.d. (µmoles) | $Cl^-$ ± s.d. (µmoles) | $Cl^-$ Rate ± s.d. (µmoles) |
| --- | --- | --- | --- | --- | --- | --- | --- |
| 0  | 19.54 ± 0.00 | 0.00 ± 0.00 | 0.00 ± 0.00 | 0.00 ± 0.00  | 0.00 ± 0.00  | 0.00 ± 0.00  | 0.00 ± 0.00 |
| 14 | 1.40 ± 0.56  | 2.84 ± 0.61 | 3.83 ± 0.51 | 5.53 ± 0.18  | 0.46 ± 0.06  | 50.88 ± 3.42 | 3.63 ± 0.24 |
| 35 | 0.03 ± 0.03  | 0.08 ± 0.05 | 1.81 ± 0.82 | 21.97 ± 0.18 | 3.30 ± 0.41  | 52.21 ± 1.30 | 1.49 ± 0.04 |
| 53 | 0.00 ± 0.00  | 0.03 ± 0.03 | 0.01 ± 0.02 | 14.04 ± 5.40 | 15.64 ± 0.91 | 63.99 ± 5.50 | 1.21 ± 0.10 |

TABLE 2

Lactate + 10% YM2

| Time (days) | PCE ± s.d. (µmoles) | TCE ± s.d. (µmoles) | DCE ± s.d. (µmoles) | VC ± s.d. (µmoles) | Ethene ± s.d. (µmoles) | $Cl^-$ ± s.d. (µmoles) | $Cl^-$ Rate ± s.d. (µmoles) |
| --- | --- | --- | --- | --- | --- | --- | --- |
| 0  | 19.54 ± 0.00 | 0.00 ± 0.00 | 0.00 ± 0.00 | 0.00 ± 0.00  | 0.00 ± 0.00  | 0.00 ± 0.00  | 0.00 ± 0.00 |
| 14 | 0.07 ± 0.08  | 0.05 ± 0.04 | 6.44 ± 0.39 | 3.79 ± 2.14  | 0.22 ± 0.38  | 61.06 ± 1.31 | 4.36 ± 0.09 |
| 35 | 0.00 ± 0.00  | 0.02 ± 0.04 | 0.24 ± 0.34 | 19.03 ± 1.25 | 10.76 ± 1.69 | 58.59 ± 1.86 | 1.67 ± 0.05 |
| 53 | 0.00 ± 0.00  | 0.02 ± 0.03 | 0.00 ± 0.00 | 0.01 ± 0.02  | 15.56 ± 1.41 | 78.09 ± 0.12 | 1.47 ± 0.00 |

TABLE 3

Lactate Control

| Time (days) | PCE ± s.d. (µmoles) | TCE ± s.d. (µmoles) | DCE ± s.d. (µmoles) | VC ± s.d. (µmoles) | Ethene ± s.d. (µmoles) | $Cl^-$ ± s.d. (µmoles) | $Cl^-$ Rate ± s.d. (µmoles) |
| --- | --- | --- | --- | --- | --- | --- | --- |
| 0  | 19.54 ± 0.00 | 0.00 ± 0.00 | 0.00 ± 0.00 | 0.00 ± 0.00 | 0.00 ± 0.00 | 0.00 ± 0.00  | 0.00 ± 0.00 |
| 14 | 8.45 ± 0.55  | 2.00 ± 0.04 | 0.42 ± 0.03 | 1.33 ± 0.41 | 0.00 ± 0.00 | 36.18 ± 2.43 | 2.58 ± 0.17 |
| 35 | 4.08 ± 0.81  | 2.77 ± 0.47 | 1.60 ± 0.82 | 3.86 ± 2.11 | 0.33 ± 0.29 | 46.47 ± 5.25 | 1.33 ± 0.15 |
| 53 | 0.33 ± 0.27  | 0.52 ± 0.47 | 5.31 ± 1.00 | 8.52 ± 6.24 | 0.78 ± 0.79 | 56.17 ± 3.17 | 1.06 ± 0.06 |

TABLE 4

No Lactate + 100 mg YM2

| Time (days) | PCE ± s.d. (µmoles) | TCE ± s.d. (µmoles) | DCE ± s.d. (µmoles) | VC ± s.d. (µmoles) | Ethene ± s.d. (µmoles) | $Cl^-$ ± s.d. (µmoles) | $Cl^-$ Rate ± s.d. (µmoles) |
| --- | --- | --- | --- | --- | --- | --- | --- |
| 0  | 19.54 ± 0.00 | 0.00 ± 0.00 | 0.00 ± 0.00 | 0.00 ± 0.00 | 0.00 ± 0.00 | 0.00 ± 0.00 | 0.00 ± 0.00 |
| 23 | 4.20 ± 0.65  | 0.16 ± 0.04 | 0.02 ± 0.02 | 0.00 ± 0.00 | 0.00 ± 0.00 | 0.20 ± 0.07 | 0.01 ± 0.00 |
| 44 | 4.27 ± 0.42  | 0.07 ± 0.03 | 0.02 ± 0.02 | 0.00 ± 0.00 | 0.00 ± 0.00 | 0.10 ± 0.08 | 0.00 ± 0.00 |

Table 5 shows the paired t-test results for the comparisons of lactate control with out YM, Lactate with 1% YM2 and Lactate with 10% Nutrient.

TABLE 5

Lactate Nutrient Ladder Paired t-test

| Bottle | Time (days) | Relative Rate wo/YM | w/1% YM2 | w/10% YM2 | |
|---|---|---|---|---|---|
| Set A 1 | 14 | 0.92 | 1.31 | 1.70 | Probability 1% YM2 > wo/YM2 |
|  | 35 | 1.11 | 1.11 | 1.21 | 99.88% |
|  | 53 | 0.96 | 1.08 | 1.39 | Probability 10% YM2 > 1% YM2 |
| 2 | 14 | 1.02 | 1.49 | 1.65 | 99.99% |
|  | 35 | 1.00 | 1.16 | 1.29 |  |
|  | 53 | 1.06 | 1.25 | 1.39 | Probability 10% YM2 > wo/YM2 |
| 3 | 14 | 1.05 | 1.42 | 1.72 | 99.99% |
|  | 35 | 0.89 | 1.11 | 1.28 |  |
|  | 53 | 0.98 | 1.08 | 1.39 |  |
| Average Relative Rate |  | 1.00 | 1.22 | 1.45 |  |

Set A Results:

All the replicates containing lactate showed good dechlorination activity. The rates of degradation were enhanced by the addition of the YM2. The reaction rate for the 10% YM2 was the fastest followed by the 1% YM2 and the Lactate Control. The YM2 as electron donor replicate demonstrated very low levels of dechlorination activity and fairly low biological activity in general. To greater than 99.88% and 99.99% probability, the 1% YM2 and 10% YM2 samples had increased dechlorination rates as compared to the Lactate Control. The Relative Rate in the 1% YM2 set was 22% faster than the Lactate Control and 45% faster in the 10% YM2 set.

Example 3

Set B: Erythorbate ML with and without YM2

The second set of microcosms used Erythorbate ML as the electron donor at 1020 mg/L initial concentration. The Erythorbate ML is the supernatant that remains after the recrystalization of Erythorbate from the mother liquor. The Erythorbate ML contains a mixture of 2 Keto-Gluconic Acid, Sodium Erythorbate and residual sugars like xylose, arabinose and succinate.

Figure 8:
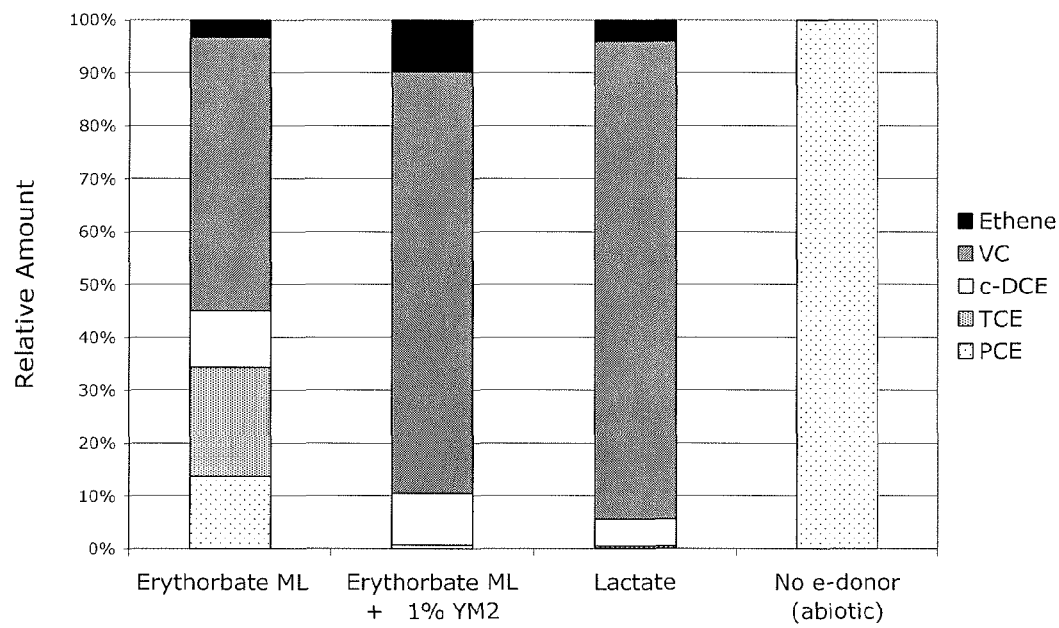
FIG. 8 shows the degradation PCE to ethene using Erythorbate ML and YM amended Erythorbate ML as the electron donor.

The objective of this set was to demonstrate that the YM2 would increase the microbial metabolic kinetics irrespective of which electron donor was used. In addition, this set was used to characterize if and to what extent Erythorbate ML was an efficacious electron donor for anaerobic bioremediation of contaminants in water. FIG. 8 shows that Erythorbate ML is capable of degrading PCE to ethene.

Tables 6-8 show the kinetic results, and include concentrations of PCE and its daughter products, Chloride generation and Chloride Rate and the associated standard deviation of results from the three bottle triplicates.

TABLE 6

Erythorbate ML 1000 mg/L

| Time (days) | PCE ± s.d. (μmoles) | TCE ± s.d. (μmoles) | DCE ± s.d. (μmoles) | VC ± s.d. (μmoles) | Ethene ± s.d. (μmoles) | Cl⁻ ± s.d. (μmoles) | Cl⁻ Rate ± s.d. (μmoles) |
|---|---|---|---|---|---|---|---|
| 0 | 19.54 ± 0.00 | 0.00 ± 0.00 | 0.00 ± 0.00 | 0.00 ± 0.00 | 0.00 ± 0.00 | 0.00 ± 0.00 | 0.00 ± 0.00 |
| 21 | 10.33 ± 0.62 | 0.80 ± 0.46 | 0.14 ± 0.07 | 2.30 ± 0.64 | 0.14 ± 0.25 | 31.87 ± 3.80 | 1.52 ± 0.18 |
| 35 | 8.26 ± 2.98 | 2.69 ± 0.97 | 0.67 ± 0.31 | 7.71 ± 3.89 | 0.53 ± 0.85 | 28.01 ± 4.59 | 0.80 ± 0.13 |
| 49 | 2.84 ± 3.25 | 4.28 ± 0.58 | 2.23 ± 0.72 | 10.71 ± 7.16 | 0.68 ± 1.10 | 38.76 ± 8.88 | 0.79 ± 0.18 |

TABLE 7

Erythorbate ML 1000 mg/L + 1% YM2

| Time (days) | PCE ± s.d. (μmoles) | TCE ± s.d. (μmoles) | DCE ± s.d. (μmoles) | VC ± s.d. (μmoles) | Ethene ± s.d. (μmoles) | Cl⁻ ± s.d. (μmoles) | Cl⁻ Rate ± s.d. (μmoles) |
|---|---|---|---|---|---|---|---|
| 0 | 19.54 ± 0.00 | 0.00 ± 0.00 | 0.00 ± 0.00 | 0.00 ± 0.00 | 0.00 ± 0.00 | 0.00 ± 0.00 | 0.00 ± 0.00 |
| 21 | 7.38 ± 1.90 | 2.00 ± 1.41 | 0.92 ± 1.09 | 2.83 ± 1.25 | 0.00 ± 0.00 | 37.98 ± 2.12 | 1.81 ± 0.10 |
| 35 | 1.41 ± 2.32 | 1.34 ± 1.69 | 4.64 ± 1.97 | 9.52 ± 4.28 | 0.00 ± 0.00 | 49.73 ± 6.79 | 1.42 ± 0.19 |
| 49 | 0.16 ± 0.15 | 0.00 ± 0.00 | 2.18 ± 3.78 | 17.94 ± 10.44 | 2.22 ± 3.16 | 55.21 ± 3.33 | 1.13 ± 0.07 |

TABLE 8

Lactate Control

| Time (days) | PCE ± s.d. (μmoles) | TCE ± s.d. (μmoles) | DCE ± s.d. (μmoles) | VC ± s.d. (μmoles) | Ethene ± s.d. (μmoles) | Cl⁻ ± s.d. (μmoles) | Cl⁻ Rate ± s.d. (μmoles) |
|---|---|---|---|---|---|---|---|
| 0 | 19.54 ± 0.00 | 0.00 ± 0.00 | 0.00 ± 0.00 | 0.00 ± 0.00 | 0.00 ± 0.00 | 0.00 ± 0.00 | 0.00 ± 0.00 |
| 21 | 7.22 ± 0.85 | 3.15 ± 0.11 | 0.83 ± 0.07 | 4.28 ± 0.44 | 0.29 ± 0.08 | 33.88 ± 2.96 | 1.61 ± 0.14 |

TABLE 8-continued

Lactate Control

| Time (days) | PCE ± s.d. (μmoles) | TCE ± s.d. (μmoles) | DCE ± s.d. (μmoles) | VC ± s.d. (μmoles) | Ethene ± s.d. (μmoles) | Cl⁻ ± s.d. (μmoles) | Cl⁻ Rate ± s.d. (μmoles) |
|---|---|---|---|---|---|---|---|
| 35 | 3.58 ± 0.90 | 3.77 ± 0.18 | 2.57 ± 0.34 | 8.37 ± 0.37 | 0.53 ± 0.12 | 39.00 ± 4.35 | 1.11 ± 0.12 |
| 49 | 0.04 ± 0.01 | 0.10 ± 0.03 | 1.31 ± 0.95 | 23.41 ± 0.34 | 1.05 ± 0.22 | 51.67 ± 1.97 | 1.05 ± 0.04 |

Table 9 shows the paired t-test results for the comparisons of Erythorbate ML with Erythorbate ML with YM2.

TABLE 9

Erythorbate ML Paired t-test

| | | Relative Rate | | |
|---|---|---|---|---|
| Bottle | Time (days) | wo/Nutrient | w/1% Nutrient | Probability 1% YM2 > wo/YM2 |
| Set B 1 | 21 | 0.81 | 1.19 | 99.89% |
| | 35 | 0.73 | 1.41 | |
| | 49 | 0.82 | 1.06 | |
| 2 | 21 | 0.98 | 1.11 | |
| | 35 | 0.60 | 1.34 | |
| | 49 | 0.55 | 1.01 | |
| 3 | 21 | 1.03 | 1.06 | |
| | 35 | 0.83 | 1.08 | |
| | 49 | 0.87 | 1.14 | |
| Average Relative Rate | | 0.80 | 1.15 | |

Figure 9:
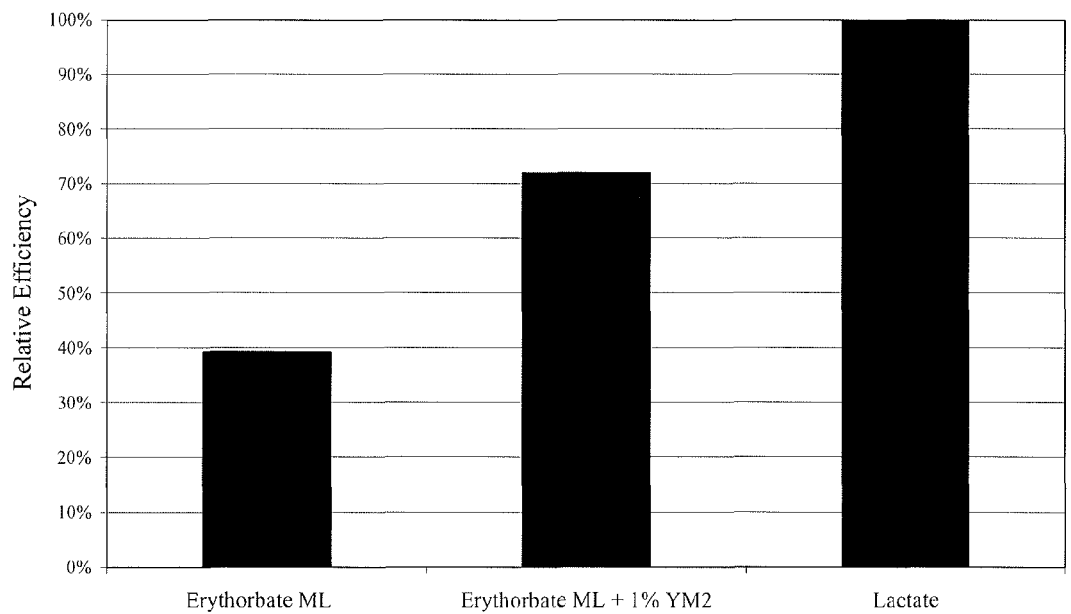
FIG. 9 show the efficiency of Erythorbate ML utilization as measured by Chemical Oxygen Demand (COD) analysis.

Table 10 and FIG. 9 show the efficiency of electron donor (e⁻) utilization as measured by COD analysis. The COD analysis calculates the utilization of electron donor by measuring the starting COD and the final COD taking the difference and converting mg/L to μmoles of electrons. The μmoles of electrons used for dechlorination was determined from the calculated Chloride produced leading to an Efficiency and Relative Efficiency of electron donor utilization as compared to lactate.

TABLE 10

Efficiency by COD analysis

| | Erythorbate ML | Erythorbate + 1% YM2 | Lactate Control |
|---|---|---|---|
| Chloride (μmoles) | 43.62 | 67.04 | 77.16 |
| Init. COD (mg/L) | 1020 | 1020 | 762 |
| Final COD (mg/L) | 867 | 894 | 566 |
| ΔCOD μmoles e⁻ | 1917 | 1579 | 1321 |
| μmoles e⁻ dechlor. | 87 | 134 | 154 |
| % of e⁻ used for dechlor. | 5.1 | 9.4 | 13.1 |
| Relative Efficiency | 39% | 72% | 100% |
| % Improvement in Efficiency with Nutrient | | 84% | |

Set B Results:

Although the Erythorbate ML dechlorination kinetics was slower than the lactate control, Erythorbate ML was an efficacious electron donor, completely dechlorinating the PCE to ethene. When comparing the bioremediation rate with and without YM2, there is better than a 99.89% probability that the Erythorbate ML with 1% YM2 was statistically faster than without YM2. The Relative Rate increased 44% with the addition of the YM2.

The Efficiency of electron donor utilization with Erythorbate was also lower as compared to lactate, but the addition of the 1% YM2 improved that utilization by 84%.

Example 4

Set C: Nutrient Comparisons

The objective of Set C was to characterize and differentiate the YM kinetics and electron donor utilization from two common, commercially available Nutrients all using 7 mmole lactate as the electron donor. The four replicates in this set included:

Lactate+10 mg/L Yeast Extract (YE)

Lactate+Vitamin Supplement optimized for anaerobic cultures based on Wolf's vitamin solution (Wolf's Mixture) provided by ATCC as a ready-to-use liquid packaged as Vitamin Supplement, catalog number MD-VS.

| TYPICAL ANALYSIS: | |
|---|---|
| | mg/liter |
| Folic acid | 2 |
| Pyridoxine hydrochloride | 10 |
| Riboflavin | 5 |
| Biotin | 2 |
| Thiamine | 5 |
| Nicotinic acid | 5 |
| Pantothenic acid | 5 |
| Vitamin B12 | 0.1 |
| p-Aminobenzoic acid | 5 |
| Thioctic acid | 5 |
| Water | 1 L |

Lactate Control

Lactate+1% YM2

Figure 10:
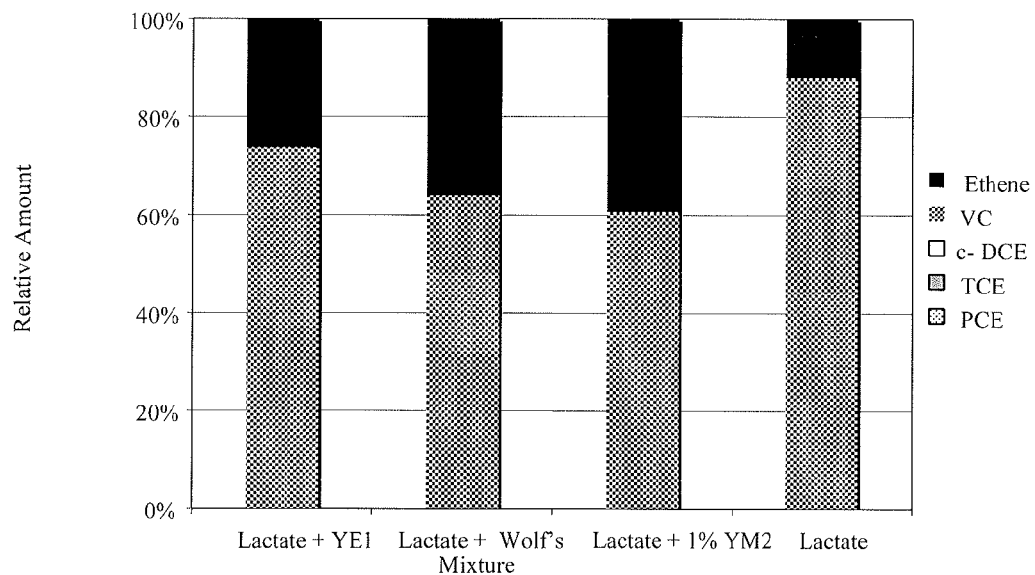
FIG. 10 shows the degradation of PCE to Ethene with lactate amended with YE, Wolf's Vitamin Mixture, and YM2.

FIG. 10 shows the rapid and complete degradation of PCE to ethene.

Tables 11-14 show the kinetic results, and include concentrations of PCE and its daughter products, Chloride generation and Chloride Rate and the associated standard deviation of results from the three bottle triplicates.

TABLE 11

Lactate + 10 mg/L YE

| Time (days) | PCE ± s.d. (μmoles) | TCE ± s.d. (μmoles) | DCE ± s.d. (μmoles) | VC ± s.d. (μmoles) | Ethene ± s.d. (μmoles) | $Cl^-$ ± s.d. (μmoles) | $Cl^-$ Rate ± s.d. (μmoles) |
|---|---|---|---|---|---|---|---|
| 0 | 19.54 ± 0.00 | 0.00 ± 0.00 | 0.00 ± 0.00 | 0.00 ± 0.00 | 0.00 ± 0.00 | 0.00 ± 0.00 | 0.00 ± 0.00 |
| 21 | 0.46 ± 0.49 | 0.70 ± 0.71 | 5.24 ± 0.76 | 10.26 ± 2.70 | 0.13 ± 0.02 | 53.48 ± 3.48 | 2.55 ± 0.17 |
| 35 | 0.10 ± 0.07 | 0.00 ± 0.00 | 1.14 ± 1.79 | 26.61 ± 2.27 | 1.05 ± 0.70 | 48.85 ± 1.83 | 1.40 ± 0.05 |
| 49 | 0.00 ± 0.00 | 0.00 ± 0.00 | 0.01 ± 0.01 | 25.97 ± 3.24 | 9.29 ± 7.00 | 52.18 ± 3.22 | 1.06 ± 0.07 |

TABLE 12

Lactate + Wolf's Mixture

| Time (days) | PCE ± s.d. (μmoles) | TCE ± s.d. (μmoles) | DCE ± s.d. (μmoles) | VC ± s.d. (μmoles) | Ethene ± s.d. (μmoles) | $Cl^-$ ± s.d. (μmoles) | $Cl^-$ Rate ± s.d. (μmoles) |
|---|---|---|---|---|---|---|---|
| 0 | 19.54 ± 0.00 | 0.00 ± 0.00 | 0.00 ± 0.00 | 0.00 ± 0.00 | 0.00 ± 0.00 | 0.00 ± 0.00 | 0.00 ± 0.00 |
| 21 | 0.00 ± 0.00 | 0.00 ± 0.00 | 4.63 ± 1.44 | 16.42 ± 4.07 | 0.43 ± 0.12 | 52.48 ± 1.47 | 2.50 ± 0.07 |
| 35 | 0.01 ± 0.01 | 0.00 ± 0.00 | 0.19 ± 0.27 | 28.21 ± 0.14 | 2.91 ± 2.65 | 49.51 ± 0.68 | 1.41 ± 0.02 |
| 49 | 0.00 ± 0.00 | 0.00 ± 0.00 | 0.00 ± 0.00 | 24.43 ± 3.27 | 13.78 ± 5.45 | 53.73 ± 3.27 | 1.10 ± 0.07 |

TABLE 13

Lactate + 1% YM2

| Time (days) | PCE ± s.d. (μmoles) | TCE ± s.d. (μmoles) | DCE ± s.d. (μmoles) | VC ± s.d. (μmoles) | Ethene ± s.d. (μmoles) | $Cl^-$ ± s.d. (μmoles) | $Cl^-$ Rate ± s.d. (μmoles) |
|---|---|---|---|---|---|---|---|
| 0 | 19.54 ± 0.00 | 0.00 ± 0.00 | 0.00 ± 0.00 | 0.00 ± 0.00 | 0.00 ± 0.00 | 0.00 ± 0.00 | 0.00 ± 0.00 |
| 21 | 0.03 ± 0.06 | 0.08 ± 0.13 | 4.29 ± 1.59 | 17.31 ± 4.11 | 0.33 ± 0.16 | 51.90 ± 0.91 | 2.49 ± 0.02 |
| 35 | 0.00 ± 0.00 | 0.00 ± 0.00 | 0.00 ± 0.00 | 27.65 ± 1.00 | 5.29 ± 1.34 | 50.51 ± 1.00 | 1.44 ± 0.03 |
| 49 | 0.00 ± 0.00 | 0.00 ± 0.00 | 0.00 ± 0.00 | 23.35 ± 2.93 | 16.37 ± 3.96 | 54.81 ± 2.93 | 1.11 ± 0.05 |

TABLE 14

Lactate Control

| Time (days) | PCE ± s.d. (μmoles) | TCE ± s.d. (μmoles) | DCE ± s.d. (μmoles) | VC ± s.d. (μmoles) | Ethene ± s.d. (μmoles) | $Cl^-$ ± s.d. (μmoles) | $Cl^-$ Rate ± s.d. (μmoles) |
|---|---|---|---|---|---|---|---|
| 0 | 19.54 ± 0.00 | 0.00 ± 0.00 | 0.00 ± 0.00 | 0.00 ± 0.00 | 0.00 ± 0.00 | 0.00 ± 0.00 | 0.00 ± 0.00 |
| 21 | 0.66 ± 0.52 | 1.20 ± 1.01 | 5.05 ± 0.62 | 10.83 ± 1.56 | 0.09 ± 0.02 | 51.01 ± 2.69 | 2.43 ± 0.13 |
| 35 | 0.00 ± 0.00 | 0.00 ± 0.00 | 2.02 ± 1.88 | 26.41 ± 2.65 | 0.54 ± 0.29 | 47.71 ± 1.16 | 1.36 ± 0.03 |
| 49 | 0.00 ± 0.00 | 0.00 ± 0.00 | 0.00 ± 0.00 | 27.74 ± 0.27 | 3.79 ± 1.31 | 50.42 ± 0.27 | 1.03 ± 0.01 |

Table 15 shows the paired t-test results for the comparisons of Lactate with Yeast Extract, Lactate with Wolf's Mixture, Lactate with 1% YM2, and Lactate Control.

TABLE 15

Lactate w/Commercial Nutrients Paired t-test

| | | | Relative Rate | | | |
|---|---|---|---|---|---|---|
| Bottle | Time (days) | Lactate Control | w/Yeast Extract | w/Wolf's Mixture | w/1% YM2 | |
| | | | | | | Probability w/1% YM2 > wo/Nutrient |
| Set C  1 | 21 | 1.06 | 0.97 | 1.06 | 1.02 | 99.50% |
| | 35 | 1.02 | 1.01 | 1.04 | 1.04 | |

TABLE 15-continued

| | | Lactate w/Commercial Nutrients Paired t-test | | | | |
|---|---|---|---|---|---|---|
| | | Relative Rate | | | | |
| Bottle | Time (days) | Lactate Control | w/Yeast Extract | w/Wolf's Mixture | w/1% YM2 | |
| | | | | | | Probability w/1% YM2 > w/Yeast Extract |
| | 49 | 1.00 | 1.00 | 1.02 | 1.03 | |
| 2 | 21 | 0.99 | 1.10 | 1.03 | 1.03 | 82.12% |
| | 35 | 0.97 | 1.07 | 1.02 | 1.08 | |
| | | | | | | Probability w/1% YM2 > w/Wolf's Mixture |
| | 49 | 0.99 | 1.11 | 1.03 | 1.10 | |
| 3 | 21 | 0.95 | 1.08 | 1.00 | 1.03 | 77.60% |
| | 35 | 1.00 | 0.99 | 1.05 | 1.05 | |
| | 49 | 1.01 | 0.99 | 1.14 | 1.11 | |
| Average Relative Rate | | 1.00 | 1.04 | 1.04 | 1.05 | |

Figure 11:
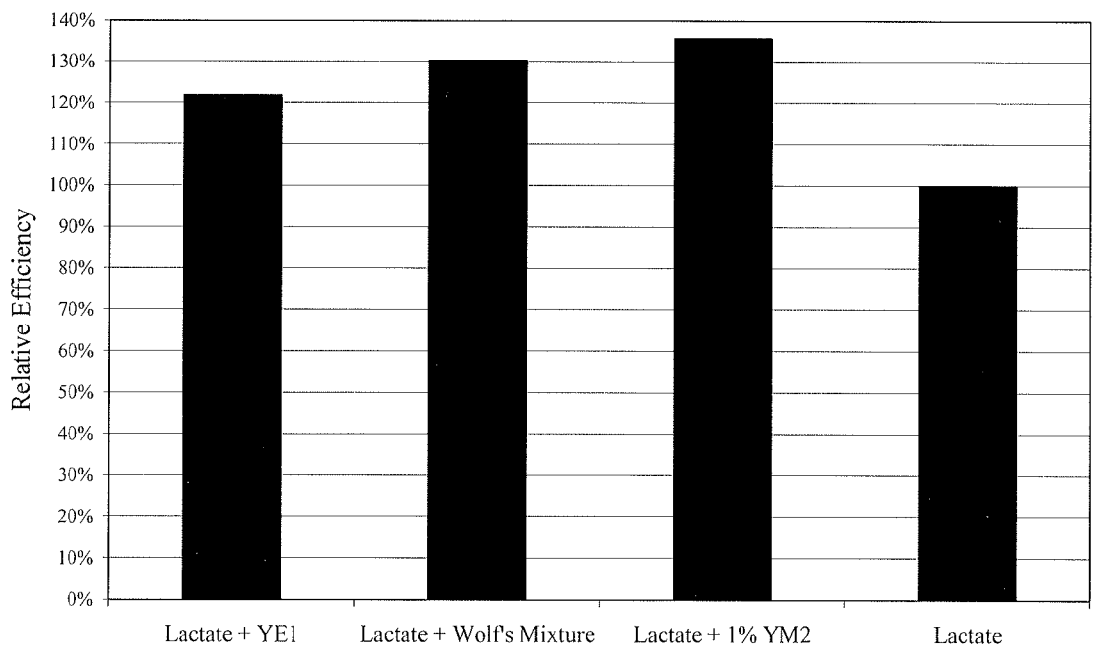
FIG. 11 shows the Relative Efficiency of the lactate amended with YE, Wolf's Vitamin Mixture, and YM2.

Table 16 and FIG. 11 show the efficiency of electron donor utilization as measured by VFA analysis. The method used to calculate the consumption of the electron donor measured the propionate, acetate and formate levels to calculate the consumption of electron donor over time. The lactate and propionate fermented very rapidly resulting in acetate and formate as the only measurable VFAs.

TABLE 16

| | Efficiency by Volatile Fatty Acid Analysis μmoles e⁻ donated by Lactate: 8400 | | | |
|---|---|---|---|---|
| (conc mM) | Lactate + Yeast Extract | Lactate + Wolf's Mixture | Lactate + 1% YM2 | Lactate Control |
| Acetate | 0.76 | 0.76 | 0.74 | 0.77 |
| Formate | 0.39 | 0.39 | 0.41 | 0.42 |
| Chloride | 120 | 128 | 134 | 98 |
| μmoles e⁻ remaining | 685 | 688 | 674 | 699 |
| μmoles e⁻ used donor | 7715 | 7712 | 7726 | 7701 |
| μmoles e⁻ used dechlor. | 240 | 257 | 268 | 197 |
| Estimated % Efficiency | 3.12 | 3.33 | 3.46 | 2.55 |
| Relative Efficiency | 1.22 | 1.30 | 1.36 | 1.00 |
| % Efficiency Improvement with 1% YM2 | | | 36% | |

FIG. 11 shows the Relative Efficiency of the lactate plus three different nutrients with lactate.

Set C Results:

All the replicates showed good dechlorination activity. The rates of degradation were enhanced by the addition of the YM2, the Yeast Extract, and the Wolf's Mixture. The reaction rate for the 1% YM2 was the fastest followed by the Wolf's Mixture, Yeast Extract, and finally the Lactate Control.

To greater than 99.50% probability, the 1% YM2 samples had increased dechlorination rates as compared to the Lactate Control. The Relative Rate of the 1% YM2 set was 5.4% faster than the Lactate Control. The improved rate of dechlorination for the 1% YM2 over the Yeast Extract and Wolf's Mixture was not statistically significant. However, the 1% YM2 improved the Relative Efficiency of lactate (electron donor) utilization by 36% as compared with the Lactate Control.

Example 5

Set D: Lactic Acid Solids

The fourth set of microcosms used Lactic Acid Solid as the electron donor at 1,150 mg/L initial concentration. Lactic Acid Solids is a mixture of lactic acid, oligimers of lactic acid and residual sugars. A typical composition of Lactic Acid Solids would be 30-50% oligimers of lactic acid, 20-50% simple sugars (maltose, dextrose, etc.) and 0-15% lactic acid.

The objective of this set was to demonstrate that the YM1 would increase the microbial metabolic kinetics for a slow release electron donor (Lactic Acid Solids). In addition, this set was used to characterize if and to what extent the Lactic Acid Solids was an efficacious electron donor for anaerobic bioremediation of contaminants in water.

Figure 12:
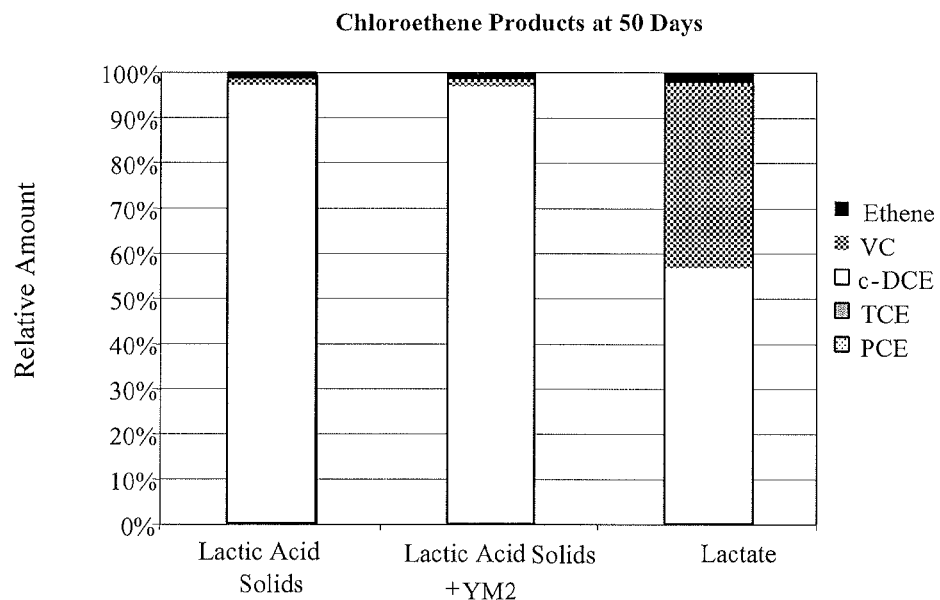
FIG. 12 shows the degradation of PCE to ethene with Lactic Acid Solids and YM amended Lactic Acid Solids.

FIG. 12 shows complete degradation of PCE to ethene although a much higher proportion of cis-DCE and lower TCE and VC than in previous sets. Because this electron donor is much higher molecular weight than the previous electron donors, the proportion of intermediate products may change, but it still leads to complete dechlorination.

Tables 17-19 show the kinetic results, and include concentrations of PCE and its daughter products, Chloride generation and Chloride Rate and the associated standard deviation of results from the three bottle triplicates.

TABLE 17

| | Lactic Acid Solids | | | | | | | |
|---|---|---|---|---|---|---|---|---|
| Time (days) | PCE ± s.d. (μmoles) | TCE ± s.d. (μmoles) | DCE ± s.d. (μmoles) | VC ± s.d. (μmoles) | Ethene ± s.d. (μmoles) | Cl⁻ ± s.d. (μmoles) | Cl⁻ Rate ± s.d. (μmoles) |
| 0 | 19.54 ± 0.00 | 0.00 ± 0.00 | 0.00 ± 0.00 | 0.00 ± 0.00 | 0.00 ± 0.00 | 0.00 ± 0.00 | 0.00 ± 0.00 |
| 22 | 0.00 ± 0.00 | 0.00 ± 0.00 | 9.25 ± 0.23 | 0.11 ± 0.00 | 0.26 ± 0.41 | 59.55 ± 0.45 | 2.71 ± 0.02 |

TABLE 17-continued

Lactic Acid Solids

| Time (days) | PCE ± s.d. (μmoles) | TCE ± s.d. (μmoles) | DCE ± s.d. (μmoles) | VC ± s.d. (μmoles) | Ethene ± s.d. (μmoles) | Cl$^-$ ± s.d. (μmoles) | Cl$^-$ Rate ± s.d. (μmoles) |
|---|---|---|---|---|---|---|---|
| 36 | 0.00 ± 0.00 | 0.03 ± 0.00 | 8.64 ± 2.53 | 0.11 ± 0.02 | 0.00 ± 0.00 | 60.69 ± 5.10 | 1.69 ± 0.14 |
| 50 | 0.00 ± 0.00 | 0.00 ± 0.00 | 5.58 ± 0.42 | 0.08 ± 0.00 | 0.08 ± 0.01 | 66.91 ± 0.84 | 1.34 ± 0.02 |

TABLE 18

Lactic Acid Solids + 10 mg/L YM1

| Time (days) | PCE ± s.d. (μmoles) | TCE ± s.d. (μmoles) | DCE ± s.d. (μmoles) | VC ± s.d. (μmoles) | Ethene ± s.d. (μmoles) | Cl$^-$ ± s.d. (μmoles) | Cl$^-$ Rate ± s.d. (μmoles) |
|---|---|---|---|---|---|---|---|
| 0 | 19.54 ± 0.00 | 0.00 ± 0.00 | 0.00 ± 0.00 | 0.00 ± 0.00 | 0.00 ± 0.00 | 0.00 ± 0.00 | 0.00 ± 0.00 |
| 22 | 0.00 ± 0.00 | 0.00 ± 0.00 | 9.03 ± 0.74 | 0.11 ± 0.01 | 0.00 ± 0.00 | 59.99 ± 1.49 | 2.73 ± 0.07 |
| 36 | 0.00 ± 0.00 | 0.03 ± 0.01 | 7.82 ± 0.64 | 0.10 ± 0.00 | 0.00 ± 0.00 | 62.31 ± 1.32 | 1.73 ± 0.04 |
| 50 | 0.00 ± 0.00 | 0.00 ± 0.00 | 4.83 ± 0.54 | 0.07 ± 0.01 | 0.08 ± 0.00 | 68.43 ± 1.08 | 1.37 ± 0.02 |

TABLE 19

Lactate Control

| Time (days) | PCE ± s.d. (μmoles) | TCE ± s.d. (μmoles) | DCE ± s.d. (μmoles) | VC ± s.d. (μmoles) | Ethene ± s.d. (μmoles) | Cl$^-$ ± s.d. (μmoles) | Cl$^-$ Rate ± s.d. (μmoles) |
|---|---|---|---|---|---|---|---|
| 0 | 19.54 ± 0.00 | 0.00 ± 0.00 | 0.00 ± 0.00 | 0.00 ± 0.00 | 0.00 ± 0.00 | 0.00 ± 0.00 | 0.00 ± 0.00 |
| 22 | 0.00 ± 0.00 | 0.00 ± 0.00 | 10.02 ± 0.06 | 0.10 ± 0.03 | 0.25 ± 0.07 | 58.02 ± 0.10 | 2.64 ± 0.00 |
| 36 | 0.00 ± 0.00 | 0.01 ± 0.02 | 7.18 ± 0.26 | 0.08 ± 0.01 | 0.23 ± 0.19 | 63.68 ± 0.46 | 1.18 ± 0.01 |
| 50 | 0.00 ± 0.00 | 0.00 ± 0.00 | 4.98 ± 0.67 | 3.57 ± 1.88 | 0.20 ± 0.09 | 64.63 ± 2.77 | 1.29 ± 0.06 |

Table 20 shows the paired t-test results for the comparisons of Lactic Acid Solids with Lactic Acid Solids plus YM1.

TABLE 20

Lactic Acid Solids Paired t-test

| | | | Relative Rate | | |
|---|---|---|---|---|---|
| Bottle | | Time (days) | wo/YM1 | w/1% YM1 | Probability w/1% YM1 > wo/YM1 |
| Set D | 1 | 22 | 1.03 | 1.03 | 92.23% |
| | | 50 | 1.03 | 1.08 | |
| | 2 | 22 | 1.03 | 1.01 | |
| | | 50 | 1.05 | 1.05 | |
| | 3 | 22 | 1.02 | 1.06 | |
| | | 36 | 1.34 | 1.49 | |
| | | 50 | 1.03 | 1.05 | |
| Average Relative Rate | | | 1.08 | 1.11 | |

Figure 13:
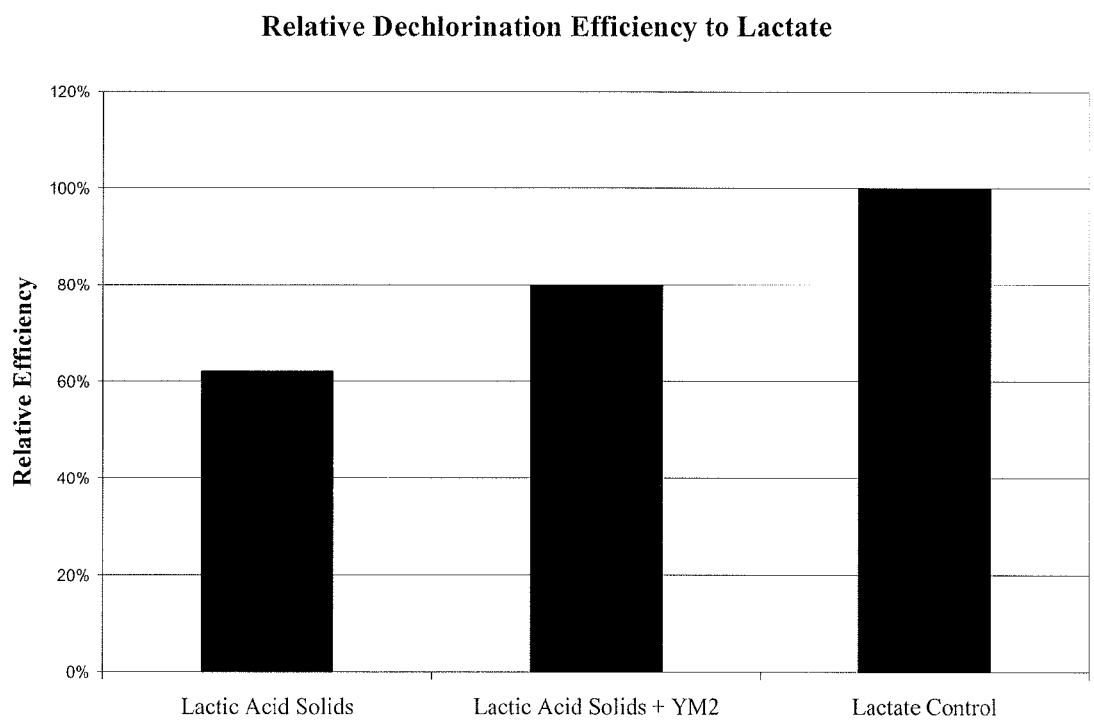
FIG. 13 shows the efficiency of Lactic Acid Solids utilization as measured by COD analysis.

Table 21 and FIG. 13 show the efficiency of electron donor utilization as measured by COD analysis.

TABLE 21

Efficiency by COD Analysis

| | Lactic Acid Solids | Lactic Acid Solids + YM1 | Lactate Control |
|---|---|---|---|
| Chloride (μmoles) | 66.91 | 68.43 | 64.63 |
| Init. COD (mg/L) | 1150 | 1150 | 960 |
| Final COD (mg/L) | 887 | 946 | 777 |
| ΔCOD μmoles e$^-$ | 3294 | 2554 | 2283 |
| μmoles e$^-$ dechlor. | 136 | 135 | 131 |
| % of e$^-$ used for dechlor. | 4% | 5% | 7% |
| Relative Efficiency | 62% | 80% | 100% |
| % Improvement in Efficiency with Nutrient | | 28% | |

Set D Results:

The Lactic Acid Solids dechlorination kinetics was faster than the lactate control and was an efficacious electron donor, completely dechlorinating the PCE to ethene. When comparing the bioremediation rate with and without YM1, there is better than a 92.23% probability that the Lactic Acid Solids with 1% YM1 was statistically faster than without YM1. The Relative Rate increased 3.2% with the addition of the YM1.

However, the YM1 improved the Efficiency of the Lactic Acid Solids (electron donor) utilization by 28% when compared with the Lactic Acid Solids without YM1.

Example 6

Set E: Relative Efficiency of Novel Bioremediation Amendments

The fifth set tested a variety of different electron donors comparing Crude Glycerin, Sodium Citrate, Ethanol and Whey all charged at nominally 1,000 mg/L to lactate at 7 mM (784 mg/L).

Figure 14:
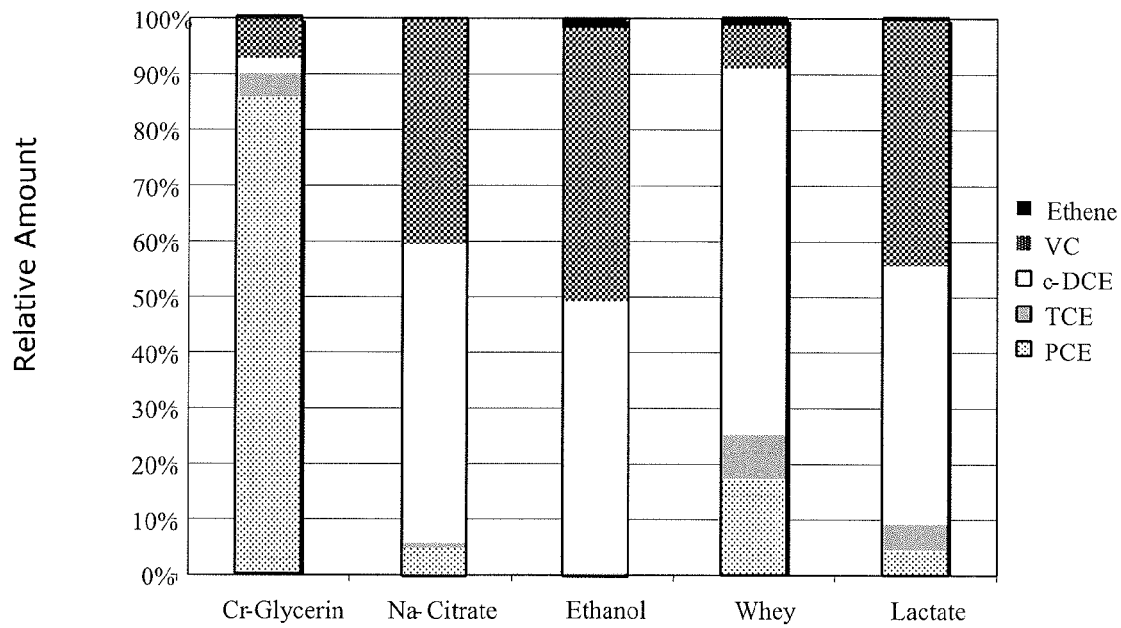
FIG. 14 shows dechlorination of PCE to ethene using Crude Glycerin, Sodium Citrate, Ethanol and Whey as compared to Lactate.
Figure 15:
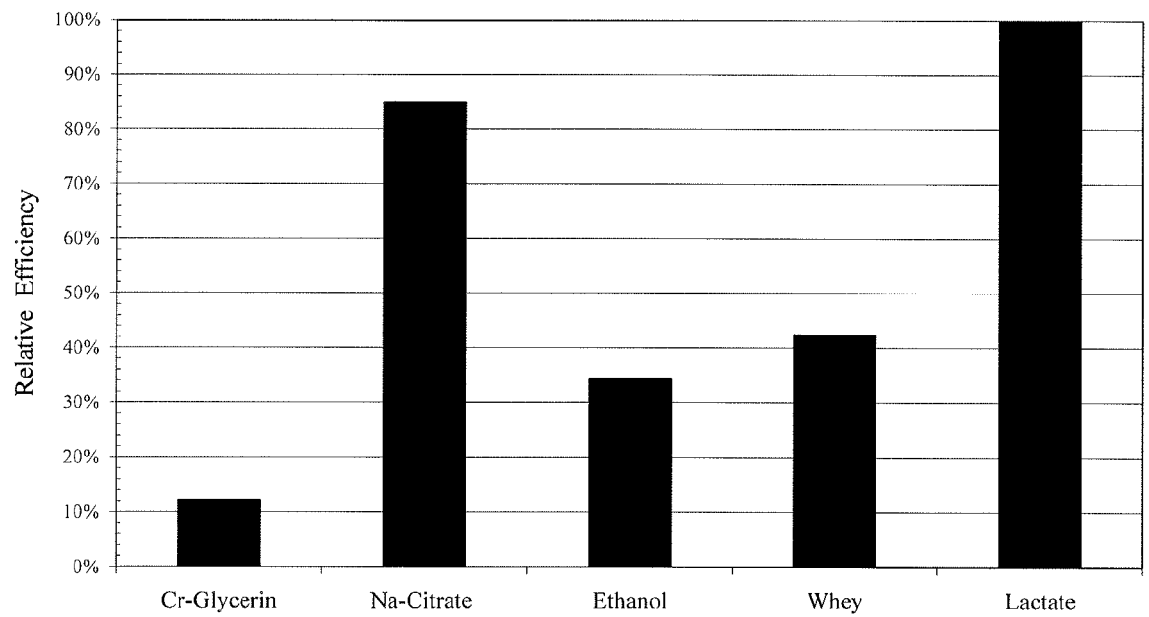
FIG. 15 shows the Relative Efficiency for the electron donors as compared to lactate.

The objective of the study was to test bioremediation amendments for efficacy as electron donors as well as to characterize their Efficiency for dechlorination as compared to the Lactate Control. FIG. 14 shows that to varying degrees all of the electron donors dechlorinated PCE through to ethene. However, Crude Glycerol was much slower than the other amendments. FIG. 15 shows the Relative Efficiency for the electron donors as compared to lactate.

Set E: Results

The two novel electron donors, Crude Glycerin and Sodium Citrate both showed the ability to completely dechlorinate PCE. The sodium citrate was almost as fast and 84% as efficient as the Lactate Control. Crude Glycerine on the other had was much slower and much of its mass was utilized for non-dechlorination processes. It was only 12% as efficient as the Lactate Control.

Example 7

Set F: Additional Novel Bioremediation Amendments

Set F included microcosms that contained Sodium Gluconate and Sodium Erythorbate. They started at concentrations that were nominally 1,000 mg/L as compared with the sodium lactate control at 7 mM (784 mg/L).

Figure 16:
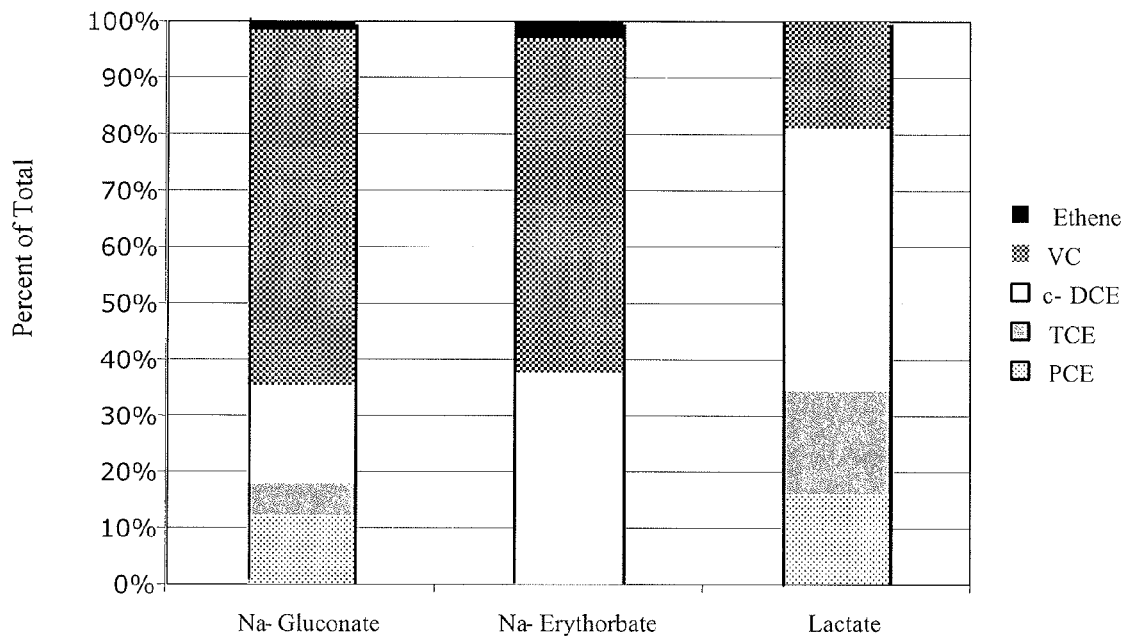
FIG. 16 shows dechlorination of PCE to ethene for Na-Gluconate and Na-Erythorbate with Lactate Control.

The objective of this set was to characterize the ability of these two novel bioremediation electron donors to completely dechlorinate PCE and characterize the electron donor utilization efficiency as compared with sodium lactate. FIG. 16 shows that at 44 days both the Na-Gluconate and the Na-Erythorbate were starting to generate Ethene.

Example 8

Set G: Additional Yeast Metabolites and Polysaccharides as Nutrients

Set G contained microcosms that tested two different Yeast Metabolites (YM3 and YM4) and a Polysaccharide (PS1) for kinetics and efficiency of electron donor utilization using lactate and molasses as the electron donors. PS1 was also tested as an electron donor by itself.

Lactate at 11.2 mM (1,000 mg/L) and nutrient amendment at 1% of the electron donor levels (~10 mg/L). Triplicate bottles received 2 micro liters of PCE and 2 ml of inoculum. The bottles were sampled 5 times over a 138 day period.

Tables 22-25 show the kinetic results and includes concentrations of PCE and its daughter products, Chloride generation and Chloride Rate and the associated standard deviation of results from the three bottle triplicates.

TABLE 22

Lactate + YM4

| Time (days) | PCE ± s.d. (µmoles) | TCE ± s.d. (µmoles) | DCE ± s.d. (µmoles) | VC ± s.d. (µmoles) | Ethene ± s.d. (µmoles) | Cl⁻ ± s.d. (µmoles) | Cl⁻ Rate ± s.d. (µmoles) |
|---|---|---|---|---|---|---|---|
| 0 | 21.57 ± 0.70 | 0.00 ± 0.00 | 0.00 ± 0.00 | 0.00 ± 0.00 | 0.00 ± 0.00 | 0.00 ± 0.00 | 0.00 ± 0.00 |
| 21 | 18.29 ± 2.45 | 4.17 ± 2.96 | 2.22 ± 1.88 | 0.10 ± 0.17 | 0.02 ± 0.03 | 8.97 ± 6.84 | 0.43 ± 0.33 |
| 35 | 8.07 ± 7.69 | 3.66 ± 2.98 | 12.70 ± 6.20 | 0.07 ± 0.13 | 0.05 ± 0.00 | 29.48 ± 9.67 | 0.84 ± 0.28 |
| 49 | 0.00 ± 0.00 | 0.00 ± 0.00 | 17.23 ± 0.86 | 0.02 ± 0.02 | 0.06 ± 0.02 | 34.76 ± 1.72 | 0.71 ± 0.04 |
| 52 | 0.00 ± 0.00 | 0.00 ± 0.00 | 21.58 ± 0.74 | 0.05 ± 0.03 | 0.06 ± 0.02 | 43.55 ± 1.54 | 0.84 ± 0.03 |
| 78 | 0.00 ± 0.00 | 0.00 ± 0.00 | 17.05 ± 2.43 | 1.31 ± 0.96 | 0.17 ± 0.04 | 38.71 ± 1.82 | 0.49 ± 0.02 |
| 138 | 0.00 ± 0.00 | 0.00 ± 0.00 | 5.43 ± 5.87 | 3.33 ± 3.12 | 5.90 ± 7.02 | 44.44 ± 9.71 | 0.32 ± 0.07 |

TABLE 23

PS1

| Time (days) | PCE ± s.d. (µmoles) | TCE ± s.d. (µmoles) | DCE ± s.d. (µmoles) | VC ± s.d. (µmoles) | Ethene ± s.d. (µmoles) | Cl⁻ ± s.d. (µmoles) | Cl⁻ Rate ± s.d. (µmoles) |
|---|---|---|---|---|---|---|---|
| 0 | 19.54 ± 0.00 | 0.00 ± 0.00 | 0.00 ± 0.00 | 0.00 ± 0.00 | 0.00 ± 0.00 | 0.00 ± 0.00 | 0.00 ± 0.00 |
| 21 | 19.44 ± 0.05 | 0.04 ± 0.06 | 0.02 ± 0.04 | 0.00 ± 0.00 | 0.04 ± 0.01 | 0.25 ± 0.14 | 0.01 ± 0.01 |
| 36 | 16.70 ± 0.46 | 0.00 ± 0.00 | 0.10 ± 0.02 | 0.00 ± 0.00 | 0.04 ± 0.01 | 0.37 ± 0.06 | 0.01 ± 0.00 |
| 50 | 11.19 ± 1.64 | 0.05 ± 0.08 | 0.04 ± 0.07 | 0.00 ± 0.00 | 0.04 ± 0.01 | 0.29 ± 0.20 | 0.01 ± 0.00 |
| 79 | 12.00 ± 2.03 | 0.04 ± 0.07 | 0.46 ± 0.13 | 0.00 ± 0.00 | 0.04 ± 0.00 | 1.12 ± 0.21 | 0.01 ± 0.00 |
| 138 | 5.03 ± 4.38 | 0.66 ± 1.14 | 2.59 ± 4.33 | 0.01 ± 0.02 | 0.03 ± 0.00 | 6.00 ± 9.86 | 0.04 ± 0.07 |

TABLE 24

Lactate + PS1

| Time (days) | PCE ± s.d. (μmoles) | TCE ± s.d. (μmoles) | DCE ± s.d. (μmoles) | VC ± s.d. (μmoles) | Ethene ± s.d. (μmoles) | $Cl^-$ ± s.d. (μmoles) | $Cl^-$ Rate ± s.d. (μmoles) |
|---|---|---|---|---|---|---|---|
| 0 | 20.87 ± 0.85 | 0.00 ± 0.00 | 0.00 ± 0.00 | 0.00 ± 0.00 | 0.00 ± 0.00 | 0.00 ± 0.00 | 0.00 ± 0.00 |
| 21 | 20.63 ± 0.67 | 0.20 ± 0.36 | 0.04 ± 0.07 | 0.00 ± 0.00 | 0.05 ± 0.00 | 0.49 ± 0.49 | 0.02 ± 0.02 |
| 36 | 13.01 ± 6.54 | 3.74 ± 2.17 | 1.79 ± 1.51 | 0.00 ± 0.00 | 0.05 ± 0.00 | 7.53 ± 4.85 | 0.21 ± 0.13 |
| 51 | 5.79 ± 4.62 | 5.02 ± 1.55 | 7.36 ± 5.77 | 0.00 ± 0.00 | 0.05 ± 0.00 | 19.94 ± 11.2 | 0.39 ± 0.22 |
| 79 | 0.00 ± 0.00 | 0.00 ± 0.00 | 20.85 ± 0.88 | 0.00 ± 0.00 | 0.05 ± 0.00 | 41.91 ± 1.77 | 0.53 ± 0.02 |
| 138 | 0.00 ± 0.00 | 0.00 ± 0.00 | 16.52 ± 0.98 | 0.01 ± 0.00 | 0.04 ± 0.00 | 33.21 ± 1.94 | 0.24 ± 0.01 |

TABLE 25

Molasses + YM3

| Time (days) | PCE ± s.d. (μmoles) | TCE ± s.d. (μmoles) | DCE ± s.d. (μmoles) | VC ± s.d. (μmoles) | Ethene ± s.d. (μmoles) | $Cl^-$ ± s.d. (μmoles) | $Cl^-$ Rate ± s.d. (μmoles) |
|---|---|---|---|---|---|---|---|
| 0 | 21.05 ± 1.64 | 0.00 ± 0.00 | 0.00 ± 0.00 | 0.00 ± 0.00 | 0.00 ± 0.00 | 0.00 ± 0.00 | 0.00 ± 0.00 |
| 21 | 20.93 ± 1.50 | 0.07 ± 0.12 | 0.02 ± 0.04 | 0.00 ± 0.00 | 0.06 ± 0.01 | 0.36 ± 0.23 | 0.02 ± 0.01 |
| 36 | 16.18 ± 5.02 | 2.20 ± 3.58 | 1.49 ± 2.31 | 0.00 ± 0.00 | 0.06 ± 0.01 | 5.42 ± 8.21 | 0.15 ± 0.23 |
| 51 | 6.93 ± 4.77 | 1.18 ± 1.96 | 4.73 ± 8.12 | 0.00 ± 0.00 | 0.06 ± 0.01 | 10.87 ± 18.2 | 0.21 ± 0.36 |
| 80 | 2.00 ± 3.47 | 0.12 ± 0.20 | 14.70 ± 12.3 | 0.00 ± 0.00 | 0.14 ± 0.04 | 30.07 ± 24.5 | 0.38 ± 0.31 |
| 138 | 1.85 ± 3.20 | 0.00 ± 0.00 | 9.54 ± 8.12 | 0.18 ± 0.28 | 0.05 ± 0.01 | 19.83 ± 16.6 | 0.14 ± 0.12 |

TABLE 26

Molasses

| Time (days) | PCE ± s.d. (μmoles) | TCE ± s.d. (μmoles) | DCE ± s.d. (μmoles) | VC ± s.d. (μmoles) | Ethene ± s.d. (μmoles) | $Cl^-$ ± s.d. (μmoles) | $Cl^-$ Rate ± s.d. (μmoles) |
|---|---|---|---|---|---|---|---|
| 0 | 19.54 ± 0.00 | 0.00 ± 0.00 | 0.00 ± 0.00 | 0.00 ± 0.00 | 0.00 ± 0.00 | 0.00 ± 0.00 | 0.00 ± 0.00 |
| 21 | 19.53 ± 0.02 | 0.00 ± 0.00 | 0.00 ± 0.00 | 0.00 ± 0.00 | 0.06 ± 0.00 | 0.26 ± 0.00 | 0.01 ± 0.00 |
| 37 | 14.10 ± 2.40 | 0.37 ± 0.03 | 0.37 ± 0.01 | 0.00 ± 0.00 | 0.06 ± 0.00 | 1.36 ± 0.05 | 0.04 ± 0.00 |
| 51 | 12.38 ± 1.56 | 0.04 ± 0.07 | 0.06 ± 0.06 | 0.00 ± 0.00 | 0.06 ± 0.00 | 0.43 ± 0.15 | 0.01 ± 0.00 |
| 80 | 11.31 ± 3.14 | 0.21 ± 0.08 | 0.52 ± 0.33 | 0.00 ± 0.00 | 0.14 ± 0.02 | 1.80 ± 0.69 | 0.02 ± 0.01 |
| 138 | 0.00 ± 0.00 | 0.00 ± 0.00 | 14.82 ± 1.81 | 0.01 ± 0.01 | 0.04 ± 0.01 | 29.82 ± 3.61 | 0.22 ± 0.03 |

TABLE 27

Lactate Control

| Time (days) | PCE ± s.d. (μmoles) | TCE ± s.d. (μmoles) | DCE ± s.d. (μmoles) | VC ± s.d. (μmoles) | Ethene ± s.d. (μmoles) | $Cl^-$ ± s.d. (μmoles) | $Cl^-$ Rate ± s.d. (μmoles) |
|---|---|---|---|---|---|---|---|
| 0 | 20.80 ± 0.95 | 0.00 ± 0.00 | 0.00 ± 0.00 | 0.00 ± 0.00 | 0.00 ± 0.00 | 0.00 ± 0.00 | 0.00 ± 0.00 |
| 21 | 18.6 ± 0.45 | 1.91 ± 0.71 | 0.31 ± 0.18 | 0.00 ± 0.00 | 0.07 ± 0.01 | 2.83 ± 1.04 | 0.13 ± 0.05 |
| 35 | 10.80 ± 1.36 | 5.91 ± 1.90 | 1.39 ± 0.72 | 0.00 ± 0.00 | 0.07 ± 0.00 | 8.95 ± 3.33 | 0.26 ± 0.10 |
| 50 | 3.13 ± 1.26 | 4.92 ± 1.03 | 9.70 ± 2.99 | 0.00 ± 0.00 | 0.07 ± 0.00 | 24.59 ± 5.08 | 0.49 ± 0.10 |
| 79 | 0.00 ± 0.00 | 0.04 ± 0.07 | 20.84 ± 0.96 | 0.00 ± 0.01 | 0.07 ± 0.00 | 42.00 ± 1.93 | 0.53 ± 0.02 |
| 138 | 0.00 ± 0.00 | 0.00 ± 0.00 | 16.55 ± 0.64 | 0.03 ± 0.03 | 0.06 ± 0.00 | 33.42 ± 1.26 | 0.24 ± 0.01 |

TABLE 28

Uninoculated Control

| Time (days) | PCE ± s.d. (μmoles) | TCE ± s.d. (μmoles) | DCE ± s.d. (μmoles) | VC ± s.d. (μmoles) | Ethene ± s.d. (μmoles) | $Cl^-$ ± s.d. (μmoles) | $Cl^-$ Rate ± s.d. (μmoles) |
|---|---|---|---|---|---|---|---|
| 0 | 19.54 ± 0.00 | 0.00 ± 0.00 | 0.00 ± 0.00 | 0.00 ± 0.00 | 0.00 ± 0.00 | 0.00 ± 0.00 | 0.00 ± 0.00 |
| 21 | 19.54 ± 0.00 | 0.00 ± 0.00 | 0.00 ± 0.00 | 0.00 ± 0.00 | 0.00 ± 0.00 | 0.00 ± 0.00 | 0.00 ± 0.00 |
| 35 | 19.54 ± 0.00 | 0.00 ± 0.00 | 0.00 ± 0.00 | 0.00 ± 0.00 | 0.00 ± 0.00 | 0.00 ± 0.00 | 0.00 ± 0.00 |

TABLE 28-continued

Uninoculated Control

| Time (days) | PCE ± s.d. (μmoles) | TCE ± s.d. (μmoles) | DCE ± s.d. (μmoles) | VC ± s.d. (μmoles) | Ethene ± s.d. (μmoles) | Cl⁻ ± s.d. (μmoles) | Cl⁻ Rate ± s.d. (μmoles) |
|---|---|---|---|---|---|---|---|
| 51 | 12.89 ± 0.81 | 0.00 ± 0.00 | 0.00 ± 0.00 | 0.00 ± 0.00 | 0.00 ± 0.00 | 0.00 ± 0.00 | 0.00 ± 0.00 |
| 79 | 14.17 ± 1.00 | 0.00 ± 0.00 | 0.07 ± 0.10 | 0.00 ± 0.00 | 0.00 ± 0.00 | 0.15 ± 0.21 | 0.00 ± 0.00 |
| 138 | 14.18 ± 1.02 | 0.10 ± 0.14 | 0.30 ± 0.43 | 0.00 ± 0.00 | 0.00 ± 0.00 | 0.70 ± 1.00 | 0.01 ± 0.01 |

TABLE 29

YM4 paired t-test

| Set G Table 1: Paired t-test | | | Relative Rate | | Probability |
|---|---|---|---|---|---|
| | Bottle | Time (days) | wo/YM4 | w/1% YM4 | w/1% YM4 > wo/YM4 |
| Set G | 1 | 21 | 0.78 | 4.14 | 99.64% |
| | | 35 | 0.63 | 3.63 | |
| | | 50 | 0.86 | 1.45 | |
| | | 79 | 1.08 | 1.65 | |
| | | 138 | 0.51 | 0.89 | |
| | 2 | 21 | 1.43 | 0.42 | |
| | | 35 | 1.37 | 2.09 | |
| | | 50 | 1.24 | 1.37 | |
| | | 79 | 1.13 | 1.69 | |
| | | 138 | 0.49 | 0.93 | |
| | 3 | 21 | 0.80 | 4.96 | |
| | | 35 | 1.00 | 4.17 | |
| | | 50 | 0.90 | 1.51 | |
| | | 79 | 1.03 | 1.77 | |
| | | 138 | 0.48 | 0.97 | |

TABLE 30

PS1 paired t-test

| Set G Table 2: Paired t-test | | | Relative Rate | | Probability |
|---|---|---|---|---|---|
| | Bottle | Time (days) | wo/PS1 | w/PS1 | w/PS1 > wo/PS1 |
| Set G | 1 | 21 | 0.78 | 0.37 | 94.56% |
| | | 35 | 0.63 | 1.20 | |
| | | 50 | 0.86 | 1.19 | |
| | | 79 | 1.08 | 1.11 | |
| | | 138 | 0.51 | 0.52 | |
| | 2 | 21 | 1.43 | 0.07 | |
| | | 35 | 1.37 | 0.22 | |
| | | 50 | 1.24 | 0.31 | |
| | | 79 | 1.13 | 1.10 | |
| | | 138 | 0.49 | 0.46 | |
| | 3 | 21 | 0.80 | 0.07 | |
| | | 35 | 1.00 | 1.04 | |
| | | 50 | 0.90 | 0.89 | |
| | | 79 | 1.03 | 1.03 | |
| | | 138 | 0.48 | 0.48 | |

TABLE 31

YM3 paired t-test

| Set G Table 3: Paired t-test | | | Relative Rate | | Probability |
|---|---|---|---|---|---|
| | Bottle | Time (days) | Molasses | Molasses + YM3 | Molasses + YM3 > Molasses |
| Set G | 1 | 21 | 0.09 | 0.07 | 95.96% |
| | | 35 | 0.15 | 0.05 | |
| | | 50 | 0.02 | 0.01 | |
| | | 79 | 0.07 | 0.05 | |
| | | 138 | 0.50 | 0.01 | |
| | 2 | 21 | 0.09 | 0.22 | |
| | | 35 | 0.14 | 1.62 | |
| | | 50 | 0.01 | 1.27 | |
| | | 79 | 0.03 | 1.17 | |
| | | 138 | 0.42 | 0.46 | |
| | 3 | 21 | 0.09 | 0.09 | |
| | | 35 | 0.14 | 0.10 | |
| | | 50 | 0.02 | 0.02 | |
| | | 79 | 0.04 | 1.07 | |
| | | 138 | 0.40 | 0.40 | |

TABLE 32

PS1, Molasses and Lactate paired t-test

| Set G Table 4: Paired t-test | | | Relative Rate | | | |
|---|---|---|---|---|---|---|
| | Bottle | Time (days) | PS1 | Molasses | Lactate | |
| | | | | | | Probability Molasses > PS1 |
| Set G | 1 | 21 | 0.07 | 0.09 | 0.78 | 98.92% |
| | | 35 | 0.05 | 0.15 | 0.63 | |
| | | 50 | 0.01 | 0.02 | 0.86 | Probability Lactate > Molasses |
| | | 79 | 0.03 | 0.07 | 1.08 | 99.996% |
| | | 138 | 0.26 | 0.50 | 0.51 | |
| | 2 | 21 | 0.05 | 0.09 | 1.43 | Probability Lactate > PS1 |
| | | 35 | 0.03 | 0.14 | 1.37 | 99.999996% |
| | | 50 | 0.02 | 0.01 | 1.24 | |
| | | 79 | 0.04 | 0.03 | 1.13 | |
| | | 138 | 0.00 | 0.42 | 0.49 | |

TABLE 32-continued

| PS1, Molasses and Lactate paired t-test | | | | |
|---|---|---|---|---|
| 3 | 21 | 0.15 | 0.09 | 0.80 |
|  | 35 | 0.04 | 0.14 | 1.00 |
|  | 50 | 0.01 | 0.02 | 0.90 |
|  | 79 | 0.02 | 0.04 | 1.03 |
|  | 138 | 0.00 | 0.40 | 0.48 |

TABLE 33

Efficiency by VFA Analysis
μmoles e⁻ donated by Lactate: 14,000 Molasses: 13,333

(conc mM)

|  | Lactate + YM4 | PS1 | Lactate + PS1 | Molasses + YM3 | Molasses | Lactate Control |
|---|---|---|---|---|---|---|
| Acetate | 3.70 | 3.54 | 3.26 | 1.79 | 2.91 | 3.78 |
| Propionate | 6.77 | 1.65 | 5.69 | 0.87 | 1.21 | 6.27 |
| Butyrate | 0.61 | 3.70 | 1.49 | 1.21 | 3.01 | 0.32 |
| Chloride | 38.70 | 1.12 | 41.91 | 30.70 | 1.80 | 42.00 |
| μmoles e⁻ remaining | 13658 | 12542 | 13554 | 5070 | 10042 | 12442 |
| μmoles e⁻ used donor | 342 | 791 | 446 | 8263 | 3291 | 1558 |
| μmoles e⁻ used dechlorination | 77.40 | 2.24 | 83.82 | 60.14 | 3.60 | 84.00 |
| Estimated % Efficiency | 22.632 | 0.283 | 18.794 | 0.728 | 0.109 | 5.392 |
| Relative Efficiency | 420% | 5% | 349% | 14% | 2% | 100% |

Set G Results

Figure 17:
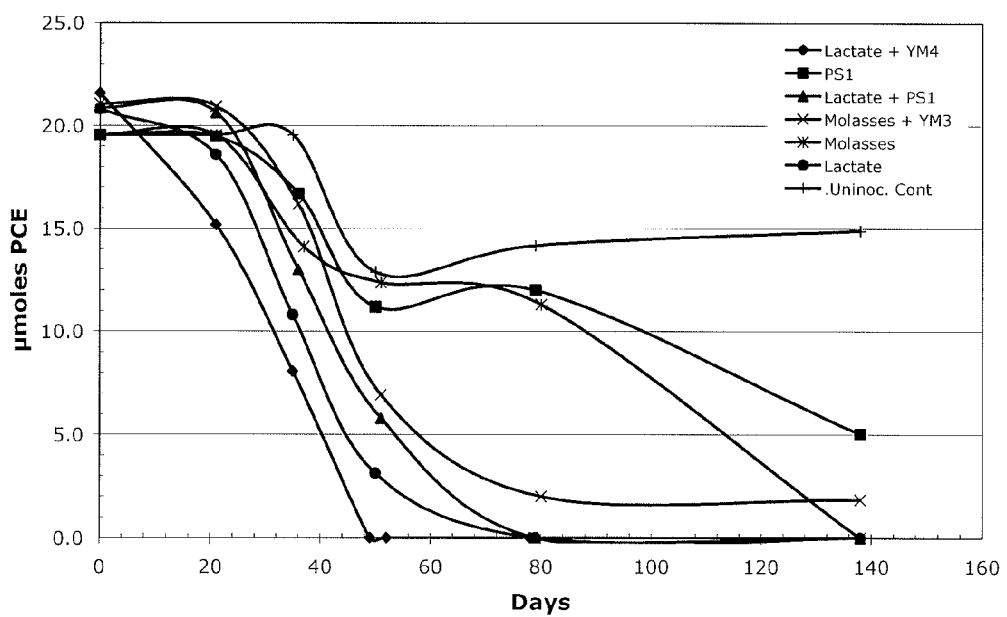
FIG. 17 shows the disappearance of PCE for a variety of yeast products and polysaccharides.
Figure 18:
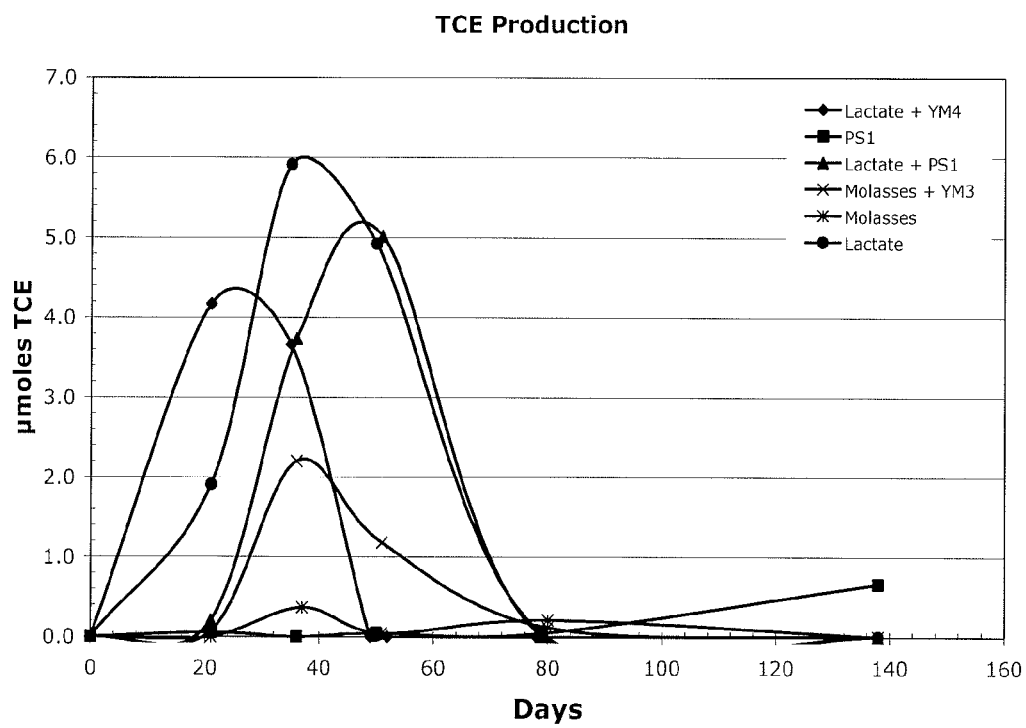
FIG. 18 shows the generation and then disappearance of TCE for a variety of yeast products and polysaccharides.
Figure 19:
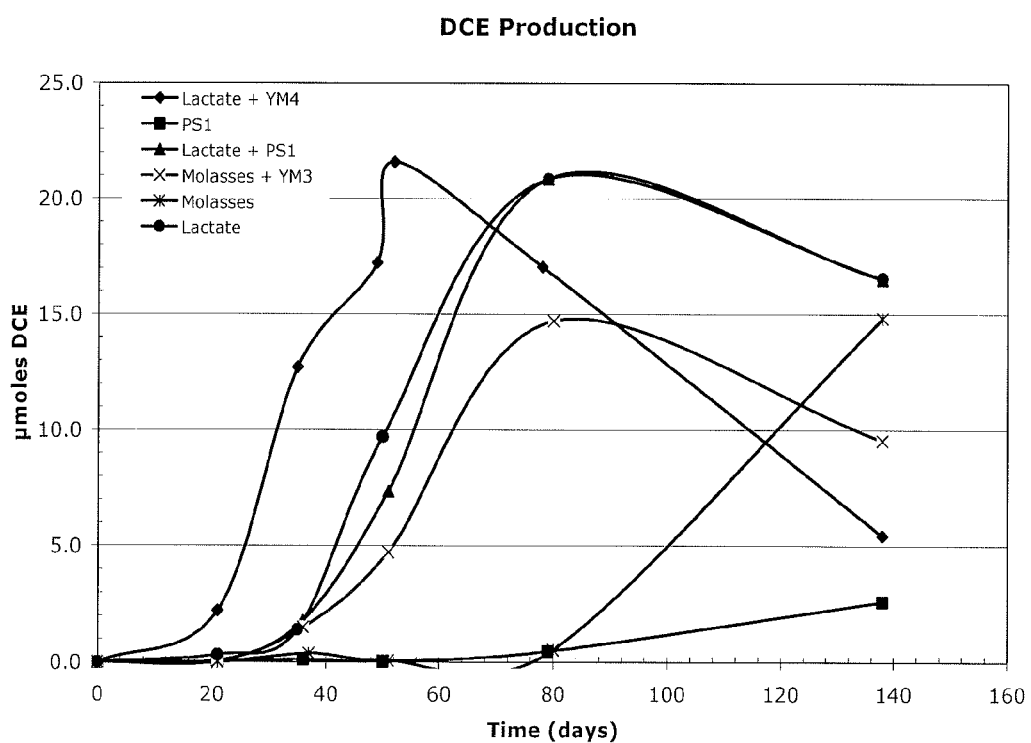
FIG. 19 shows the generation and then disappearance of DCE for a variety of yeast products and polysaccharides.
Figure 20:
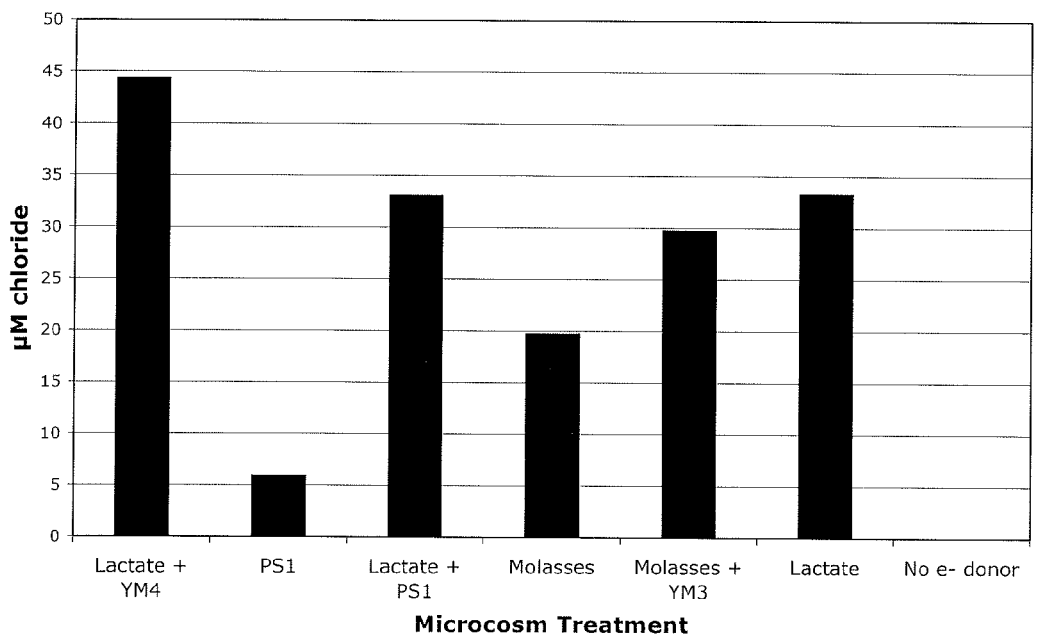
FIG. 20 shows the total dechlorination through 138 days for a variety of yeast products and polysaccharides as measured by chloride generation.

FIGS. 17-19 show the disappearance of lactate, the generation and disappearance of TCE and the generation and disappearance of cis-DCE respectively. The PS1 and Molasses both sugars had a significant 80 day lag before significant PCE degradation occurred. The lactate plus YM4 degraded the PCE, TCE and cis-DCE the fastest.

FIG. 18 shows the cumulative chloride generation based on dechlorination of the PCE and daughter products. The lactate+YM4 had the most complete dechlorination through 138 days followed by the lactate+PS1 and the lactate control which were statistically the same.

Because of the lag in the PS1 and molasses, they had the least complete dechlorination through 138 days. Addition of the YM3 to the molasses increased the dechlorination kinetics significantly.

Tables 29-31 show that the YM4, PS1 and YM3 all generated statistically significant increases in dechlorination kinetics.

Table 32 showed that Lactate was statistically higher dechlorination kinetics as compared to PS1 and molasses.

Figure 21:
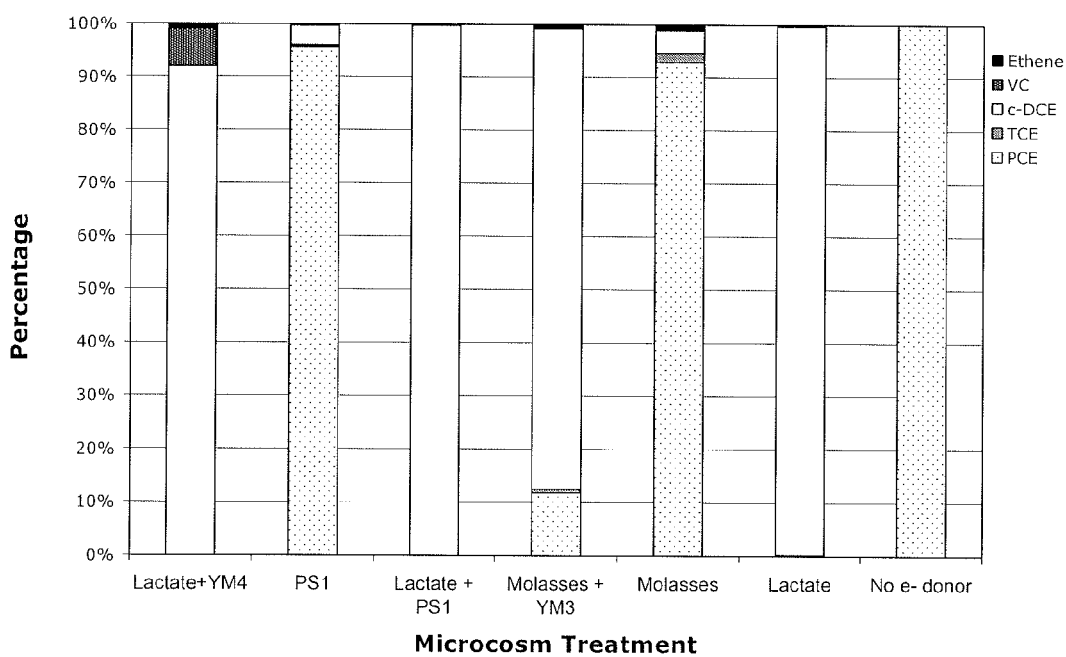
FIG. 21 shows the relative proportion of chlorethenes at 80 days for a variety of yeast products and polysaccharides.
Figure 22:
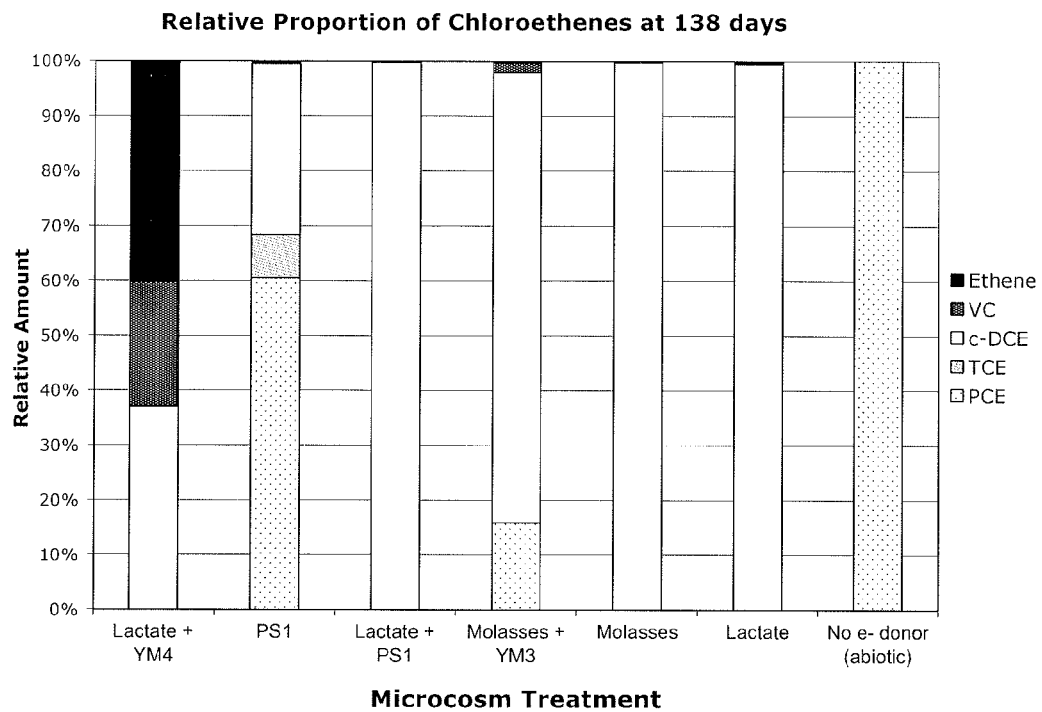
FIG. 22 shows the relative proportion of chlorethenes at 138 days for a variety of yeast products and polysaccharides.

FIGS. 21 and 22 show the relative proportion of chloroethenes present at 80 and 138 days. They show that the YM4 amended lactate performed the best and that the YM3 amended molasses outperformed the unamended molasses.

Table 33 showed that Lactate was statistically more efficient an electron donor as compared to PS1 and molasses. It also shows that YM4 and PS1 amended electron donors are much more efficient than their unamended counterparts.

Figure 23:
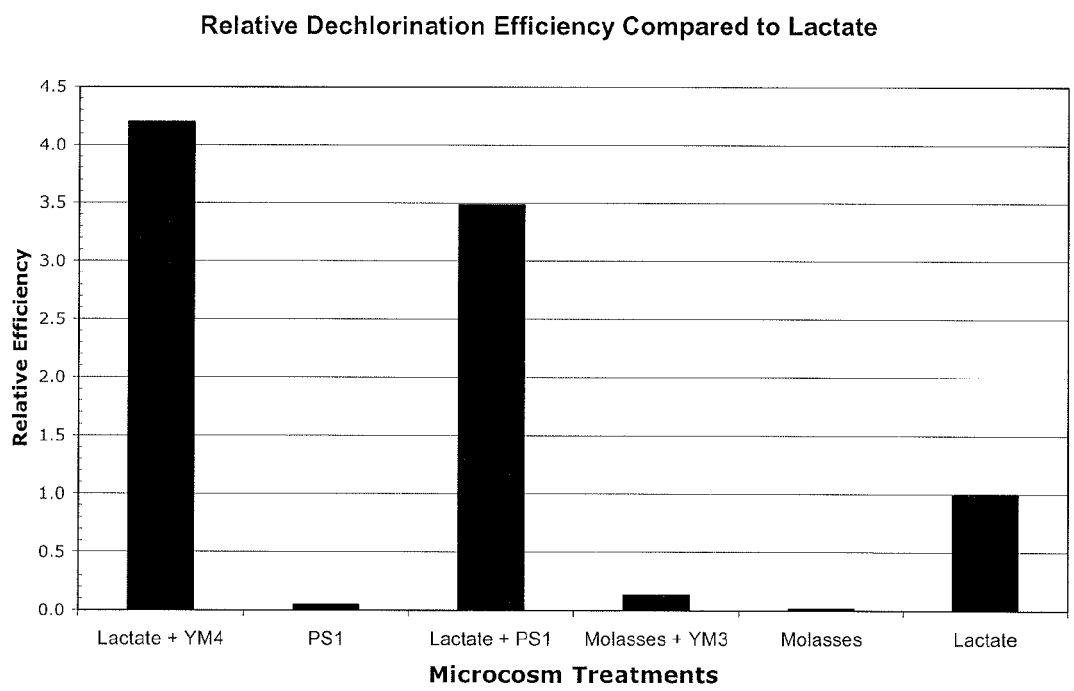
FIG. 23 shows the relative dechlorination efficiency for a variety of yeast products and polysaccharides.

FIG. 23 shows the efficiency of electron donor utilization for dechlorination. All of the non-lactate microcosms showed very poor utilization of electron donor for dechlorination. Addition of PS1 and YM4 to lactate both increased the efficiency of electron donor utilization over the lactate control.

LIST OF REFERENCES

The following references and patents and publication of patent applications are either cited in this disclosure or are of relevance to the present disclosure. All documents listed below, along with other papers, patents and publication of patent applications cited throughout this disclosures, are hereby incorporated by reference as if the full contents are reproduced herein:

Beharka, A. A., and T. G. Nagaraja. 1991. Effects of *Aspergillus oryzae* extract (AMAFERM) on ruminal fibrolytic bacteria and in vitro fiber degradation. Page 32 in Abstracts of 21st Biennial Conference on Rumen Function. Chicago, Ill.

Bennet, et al, "Evaluating Lactate Utilization In Situ: Sulfate Reduction Versus Reductive Dechlorination" (platform abstract), Seventh Annual In-Situ and On-Site Bioremediation Conference, Battelle, Jun. 4, 2003.

Bouwer, et al, "Transformations of 1- and 2-Carbon Halogenated Aliphatic Organic Compounds Under Methanogenic Conditions," Applied and Environmental Microbiology, April 1983 pp. 1286-1294.

Callaway, E. S. and S. A. MARTIN. Effects of a *Saccharomyces cerevisiae* Culture on Ruminal Bacteria that Utilize Lactate and Digest Cellulose. Journal of Dairy Science Vol. 80, No. 9, 1997

Capiro, et al, "Spacial Variability of Dechlorination Activity Within a PCE DNAPL Source-Zone" (platform abstract), Seventh Annual In-Situ and On-Site Bioremediation Conference, Battelle, Jun. 4, 2003.

Carr, et al, "Effect of Dechlorinating Bacteria on the Longevity and Composition of PCT-Containing Nonaqueous Phase Liquids under Equilibrium Dissolution Conditions," Environmental Science & Technology, vol. 34, No. 6, 2000 pp. 1088-1094.

DiStefano, et al, "Hydrogen as an Electron Donor for Dechlorination of Tetrachloroethene by an Anaerobic Mixed Culture," Applied and Environmental Microbiology, November 1992 pp. 3622-3629.

DiStefano, et al, "Reductive Dechlorination of High Concentration of Tetrachoroethene to Ethene by an Anaerobic Enrichment Culture in the Absence of Methanogenesis," Applied and Environmental Microbiology, August 1991 pp. 2287-2292.

Fennel, et al, "Assessment of Indigenous Reductive Dechlorinating Potential as a TCE-Contaminated Site Using Microcosms, Polymerase Chain Reaction Analysis, and Site Data", Environmental Science & Technology, vol. 35, no. 9, pp 1830-1839.

Fennell, et al., "Comparison of Butyric Acid, Lactic Acid, and Propionic Acid as Hydrogen Donors for the Reductive Dechlorination of Tetrachloroethene," Environmental Science & Technology, vol. 31, No. 3, 1997 pp. 918-926.

Fennell, et al, "Enrichment of High-Rate PCE Dechlorination and Comparative Study of Lactate, methanol, and hydrogen as Electron Donors to Sustain Activity", Environmental Science & Technology, vol. 33, no. 15, pp 2681-2682.

Fennell, et al, "Modeling the Production of and Competition for Hydrogen in a Dechlorinating Culture," Environmental Science & Technology, vol. 32, No. 16, 1998 pp. 2450-2460.

Freedman, et al., "Biological Reductive Dechlorination of Tetrachloroethylene and Trichloroethylene to Ethylene under Methanogenic Conditions," Applied and Environmental Microbiology, September 1989 pp. 2144-2151.

Holliger, et al, "A Highly Purified Enrichment Culture Couples the Reductive Dechlorination of Tetrachloroethene to Growth," Applied and Environmental Microbiology, September 1993 pp. 2991-2997.

Howze, "Test at TAN Bioremediation of Groundwater Plume Shows Promise," iNEWs, Jul. 6, 1999.

Lewis, et al, "In Situ Bioremediation of PCE Using Lactate" (platform abstract), Seventh Annual In-Situ and On-Site Bioremediation Conference, Battelle, Jun. 2, 2003.

Major, et al, "Discussion of Environment vs. Bacteria or Let's Play, 'Name that Bacteria'", Ground Water Monitoring & Remediation, vol. 23, no. 2, pp 32-48.

Major, et al, "Short Course: Bioaugmentation to Remediate Chlorinated Solvents in Groundwater" (PowerPoint presentation), Seventh Annual In-Situ and On-Site Bioremediation Conference, Battelle, Jun. 4, 2003.

Martin, Jennifer P., "Field Evaluation of Microbial Competition During Large Scale Enhanced TCE Dechlorination" (platform abstract), Seventh Annual In-Situ and On-Site Bioremediation Conference, Battelle, Jun. 2, 2003.

Maymo-Gatell, et al, "Isolation of a Bacterium That Reductively Dechlorinates Tetrachoroethene to Ethene," Science, vol. 276, pp. 1568-1571.

McCray, et al, "Cyclodextrin-Enhanced Solubilization of Organic Contaminants with Implications for Aquifer Remediation," Winter 2000 GWMR, pp. 94-103.

Miller-Webster, T., W. H. Hoover, M. Holt and J. E. Nocek. 2002. Influence of Yeast Culture on Ruminal Microbial Metabolism in Continuous Culture. J. Dairy Sci. 85:2009-2014

Newbold, C. J., R. J. Wallace, X. B. Chen, and F. M. McIntosh. 1995 Different strains of Saccharomyces cerevisiae differ in their effects on ruminal bacterial numbers in vitro and in sheep. J. Anim. Sci. 73:1811-1819.

Nisbet, D. J. and S. A. Martin. Effect of a Saccharomyces cerevisiae culture on lactate utilization by the ruminal bacterium Selenomonas ruminantium. J Anim Sci 1991. 69:4628-4633.

Pawan, et al, "Evaluation of Remedial Technologies to Treat Chloroethenes in Groundwater" (platform abstract), Seventh Annual In-Situ and On-Site Bioremediation Conference, Battelle, Jun. 2, 2003.

Raymond, et al, "Cost Implications of Hydrogen Donor Selection for In0Situ Bioremediation of Chlorinated Solvents", Seventh Annual In-Situ and On-Site Bioremediation Conference, Battelle, June 2003.

Rockne, K. J. and K. R. Reddy, BIOREMEDIATION OF CONTAMINATED SITES, International e-Conference on Modern Trends in Foundation Engineering: Geotechnical Challenges and Solutions, Indian Institute of Technology, Madras, India, October 2003.

Romer, et al, "Large-Scale Lactate Injection in a Mildly Reducing Aquifer for PCE Dechlorination" (platform abstract), Seventh Annual In-Situ and On-Site Bioremediation Conference, Battelle, Jun. 4, 2003.

Sorenson, Kent S., "Chlorinated Solvents Bioavailability Enhancement Technology" (PowerPoint presentation), North Wind Environmental, Inc., Remediation Technology Division.

Sorenson, Kent S., "Enhanced In Situ Bioremediation of a TCE Source Area" (PowerPoint presentation, selected slides), North Wind Environmental, Inc., Remediation Technology Division.

Sorenson, Kent S., "Field Scale Enhanced In Situ Reductive Dechlorination of TCE—Lessons from 3 Years of Operations at INEEL Test Area North Site" (PowerPoint presentation, selected slides), North Wind Environmental, Inc., Remediation Technologies Division.

Sorenseon, K. S., "Intrinsic and Enhanced In Situ Biodegradation of Trichloroethene in Deep, Fractured Basalt Aquifer," Dissertation, May 2000.

Vogel, et al, "Biotransformation of Tetrachloroethylene to Trichloroethylene, Dichloroethylene, Vinyl Chloride, and Carbon Dioxide under Methanogenic Conditions," Applied and Environmental Microbiology, May 1985 pp. 1080-1083.

Wiedmeier, R. D., M. J. Arambel, and J. L. Walters. 1987. Effects of yeast culture and Aspergillus oryzae fermentation extract on ruminal characteristics and nutrient digestion. J. Dairy Sci. 70:2063-2068.

Williams, P. E., C. A. Tait, G. M. Innes and C. J. Newbold Effects of the inclusion of yeast culture (Saccharomyces cerevisiae plus growth medium) in the diet of dairy cows on milk yield and forage degradation and fermentation patterns in the rumen of steers. J Anim Sci 1991. 69:3016-3026.

Patents and Patent Applications

| U.S. Patent Documents | | |
|---|---|---|
| 6,783,678 | August 2004 | Sorenson et al. |
| 7,045,339 | May 2006 | Sorenson et al. |
| 5,554,290 | September 1996 | Suthersan |
| 7,138,059 | November 2006 | Sorenson et al. |
| 4,585,482 | April 1986 | Tice et al. |
| 5,264,018 | November 1993 | Koenigsberg et al. |
| 5,277,815 | January 1994 | Beeman |
| 5,395,419 | March 1995 | Farone et al. |
| 5,434,241 | July 1995 | Kim et al. |

U.S. Patent Documents

| | | |
|---|---|---|
| 5,464,771 | November 1995 | Bryant et al. |
| 5,516,688 | May 1996 | Rothmel |
| 5,560,904 | October 1996 | Laugier et al. |
| 5,587,317 | December 1996 | Odom |
| 5,658,795 | August 1997 | Kato et al. |
| 5,833,855 | November 1998 | Saunders |
| 5,840,571 | November 1998 | Beeman et al. |
| 5,932,472 | August 1999 | Abdullah |
| 5,993,658 | November 1999 | Kato et al. |
| 6,001,252 | December 1999 | Rice et al. |
| 6,265,205 | July 2001 | Hitchens et al. |
| 6,420,594 | July 2002 | Farone et al. |
| 6,472,198 | October 2002 | Semprini et al. |
| 6,562,235 | May 2003 | Newell et al. |
| 6,589,776 | July 2003 | Harkness |
| 5,602,296 | February 1997 | Hughes et al. |
| 5,071,754 | December 1991 | Walkup et al. |
| 5,006,250 | April 1991 | Roberts et al. |
| 4,401,569 | August 1983 | Jahaveri et al. |
| 5,200,343 | April 1993 | Cole et al. |
| 5,342,769 | August 1994 | Hunter et al. |
| 5,753,122 | May 1998 | Taylor et al. |
| 5,910,245 | June 1999 | Bernhardt et al. |
| 5,766,929 | June 1998 | Orolin et al. |

Foreign Patent Documents

| | | |
|---|---|---|
| WO 99/24367 | May, 1999 | WO |

We claim:

1. A composition for bioremediation of a contaminated material comprising a bioremediation enhancing agent in an amount effective to enhance bioremediation of said contaminated material, wherein said bioremediation enhancing agent is a yeast metabolite present in said composition in a dosage sufficient to achieve a final yeast metabolite concentration of about 0.1 mg to about 500 mg per liter of contaminated material when said composition is added to said contaminated material, said yeast metabolite being prepared from live yeast cells, wherein said live yeast cells have been grown to exponential phase under an aerobic condition before being shifted to an anaerobic condition and grown for at least 15 minutes under said anaerobic condition.

2. The composition of claim 1, wherein the bioremediation enhancing agent further comprises at least one polysaccharide.

3. The composition of claim 1 further comprising at least one electron donor.

4. The composition of claim 3, wherein said at least one electron donor comprises at least one member selected from the group consisting of alcohol, C2-C6 carboxylic acids and salts or esters or polymers thereof, C2-C6 hydroxy acids and salts or esters or polymers thereof, volatile fatty acids and salts or esters thereof, molasses, sugars, vegetable oil, emulsified vegetable oil substrates, free fatty acids, fatty acid esters, glycerol tripolylactate, a hydrogen release compound, whey powder, corn syrup, and combinations thereof.

5. The composition of claim 1, wherein said effective amount is an amount sufficient to increase the kinetics of bioremediation when compared with a bioremediation reaction without the addition of said bioremediation enhancing agent.

6. The composition of claim 1, wherein said effective amount is an amount of said bioremediation enhancing agent that improves by at least 5% the efficiency of electron donor utilization when compared with a bioremediation reaction without the addition of said bioremediation enhancing agent.

7. The composition of claim 2, wherein the at least one polysaccharide comprises at least one member selected from the group consisting of beta-glucan, yeast-derived polysaccharides, oligosaccharides, glycans, cellulose, starch, glycogen, chitin, and mixtures thereof.

8. The composition of claim 3, wherein said at least one electron donor comprises at least one member selected from the group consisting of gluconic acid and salts thereof, erythorbate and salts thereof, erythorbate mother liquor, crude glycerol, citric acid and salts thereof, lactic acid solids of various molecular weight distributions, and combinations thereof.

9. The composition of claim 1 further comprising at least one organic acid.

10. The composition of claim 9, wherein said at least one organic acid is produced by a fermentation process.

11. The composition of claim 10, wherein said composition further comprises at least one residual nutrient that is carried over from said fermentation process.

12. The composition of claim 10, wherein said composition further comprises at least one carbohydrate that is carried over from said fermentation process.

13. The composition of claim 10, wherein said at least one organic acid comprises lactic acid.

14. The composition of claim 13, wherein said at least one organic acid is produced by a lactic acid microorganism by said fermentation process.

15. The composition of claim 1, wherein said composition is in a liquid form.

16. The composition of claim 3, wherein said effective amount is an amount sufficient to improve the efficiency of electron donor utilization when compared with a bioremediation reaction without the addition of said bioremediation enhancing agent.

17. The composition of claim 4, wherein said alcohol is a member selected from the group consisting of glycerol and ethanol.

18. A method for bioremediation of a contaminated material, comprising the step of adding to said contaminated material the composition of claim 1.

19. The method of claim 18, wherein said effective amount is selected from the group consisting of an amount sufficient to improve the efficiency of electron donor utilization and an amount sufficient to increase the kinetics of bioremediation when compared with a bioremediation reaction without the addition of said bioremediation enhancing agent.

20. The method of claim 19, wherein said effective amount is an amount of said bioremediation enhancing agent that improves by at least 5% the efficiency of electron donor utilization when compared with a bioremediation reaction without the addition of said bioremediation enhancing agent.

21. The method of claim 19, wherein said effective amount is an amount of said bioremediation enhancing agent that increases by at least 2% the kinetics of bioremediation when compared with a bioremediation reaction without the addition of said bioremediation enhancing agent.

22. The method of claim 18, wherein the bioremediation enhancing agent further comprises at least one polysaccharide.

23. The method of claim 22, wherein the at least one polysaccharide comprises at least one member selected from the group consisting of beta-glucan, yeast-derived polysaccharides, oligosaccharides, glycans, cellulose, starch, glycogen, chitin, and mixtures thereof.

24. The method of claim 18, wherein the contaminated material comprises a halogen-containing chemical.

25. The method of claim 24, wherein the halogen-containing chemical is selected from the group consisting of halogenated aliphatic hydrocarbon and halogenated aromatic hydrocarbon.

26. The method of claim 18, wherein the contaminated material comprises non-halogen-containing chemical, said non-halogen-containing chemical comprising aliphatic hydrocarbon and non-halogenated aromatic hydrocarbon, wherein said non-halogenated aromatic hydrocarbon includes at least one compound selected from the group consisting of benzene, toluene, ethylbenzene, and xylene.

27. The method of claim 18, wherein the contaminated material comprises a chemical selected from the group consisting of perchlorate salts, pesticides, metals, nitrates, sulfates, MTBE, industrial or municipal waste water, polychlorinated biphenyls, acid mine drainage, radio-nucleotides and dioxins.

28. The method of claim 18 further comprising a step of adding bacteria to the contaminated material.

29. The method of claim 28, wherein the bacteria are halo-respiring.

30. The method of claim 28, wherein the bacteria are aerobic.

31. The method of claim 28, wherein the bacteria are anaerobic.

32. The method of claim 18 further comprising a step of adding to said contaminated material at least one electron donor.

33. The method of claim 32, wherein said at least one electron donor comprises at least one member selected from the group consisting of C2-C6 carboxylic acids and salts or esters or polymers thereof, C2-C6 hydroxy acids and salts or esters or polymers thereof, volatile fatty acids and salts or esters thereof, molasses, sugars, vegetable oil, emulsified vegetable oil substrates, free fatty acids, fatty acid esters, glycerol tripolylactate, HRC®, HRC-X®, HRC Advanced®, whey powder, corn syrup, and combinations thereof.

34. The method of claim 32, wherein said at least one electron donor comprises at least one member selected from the group consisting of gluconic acid and salts thereof, erythorbate and salts thereof, erythorbate mother liquor, crude glycerol, citric acid and salts thereof, lactic acid solids of various molecular weight distributions, and combinations thereof.

35. The method of claim 18, wherein the bioremediation of said contaminated material is conducted under an aerobic condition.

36. The method of claim 18, wherein the bioremediation of said contaminated material is conducted under an anaerobic condition.

37. The method of claim 18 further comprising a step of adding to said contaminated material at least one electron acceptor.

38. The method of claim 37, wherein said at least one electron acceptor comprises at least one member selected from the group consisting of oxygen, sulfate, nitrate, peroxide, oxidizing agents, permanganates, ozone, compounds that chemically or biologically generate oxygen, metallic peroxygens, ORC®, ORC-Advanced®, RegenOx™ and mixtures thereof.

39. The method of claim 18 further comprising a step of adding to said contaminated material a mixture of at least one organic acid, said mixture comprising residual nutrients that are carried over from a fermentation process that is used to produce said at least one organic acid.

* * * * *